United States Patent
Gray et al.

(10) Patent No.: US 11,668,715 B2
(45) Date of Patent: Jun. 6, 2023

(54) BIOMARKERS OF DISEASE

(71) Applicant: Edith Cowan University, Joondalup (AU)

(72) Inventors: Elin Gray, Iluka (AU); Pauline Zaenker, Currambine (AU); Mel Ziman, Sorrento (AU); Johnny Su Hau Lo, Landsdale (AU)

(73) Assignee: Edith Cowan University, Western (AU)

( * ) Notice: Subject to any disclaimer, the term of this patent is extended or adjusted under 35 U.S.C. 154(b) by 596 days.

(21) Appl. No.: 16/615,687

(22) PCT Filed: May 22, 2018

(86) PCT No.: PCT/AU2018/050492
§ 371 (c)(1),
(2) Date: Nov. 21, 2019

(87) PCT Pub. No.: WO2018/213877
PCT Pub. Date: Nov. 29, 2018

(65) Prior Publication Data
US 2020/0116722 A1 Apr. 16, 2020

(30) Foreign Application Priority Data
May 22, 2017 (AU) .................... 2017901921

(51) Int. Cl.
G01N 33/00 (2006.01)
G01N 33/574 (2006.01)
G01N 33/564 (2006.01)

(52) U.S. Cl.
CPC ....... G01N 33/5743 (2013.01); G01N 33/564 (2013.01)

(58) Field of Classification Search
CPC .................... G01N 33/5743; G01N 33/564
See application file for complete search history.

(56) References Cited

U.S. PATENT DOCUMENTS

2010/0144055 A1   6/2010  Holzman et al.
2014/0335082 A1* 11/2014  Dransfield ........... A61K 31/337
                                                      424/133.1

FOREIGN PATENT DOCUMENTS

| WO | WO 03/074007 A2 | 9/2003 |
|---|---|---|
| WO | WO 2008/141615 A1 | 11/2008 |
| WO | WO 2010/065944 A1 | 6/2010 |
| WO | WO2010065944 | * 10/2010 |
| WO | WO 2014/018903 A1 | 1/2014 |
| WO | WO2010/065944 | * 6/2020 |

OTHER PUBLICATIONS

Angelopoulou et al (Int J Cancer 58: 480-487, 1994) (Year: 1994).*
Zaenker P., et al., "Serologic autoantibodies as diagnostic cancer biomarkers—a review". Cancer Epidemiology, Biomarkers & Prevention, 2013, vol. 22, No. 12: pp. 2161-2181).
Zaenker P., et al., "Autoantibody Production in Cancer—The Humoral Immune Response toward Autologous Antigens in Cancer Patients." Autoimmunity Reviews, 2016, vol. 15: pp. 477-483.
Search Report, Corresponding European Application No. 18805200.5 dated Jan. 27, 2021.
Huang et al., 1998, Journal of Investigative Dermatology, 111(4):662-667.
Widom et al., 1997, Gene, 198(1-2):407-420.
Zippeeius et al., 2006, Cancer Immunology, Immunotherapy, 56(2):249-258.

* cited by examiner

*Primary Examiner* — Lei Yao
(74) *Attorney, Agent, or Firm* — Morgan, Lewis & Bockius LLP

(57) ABSTRACT

The present invention relates to methods for the diagnosis and treatment of melanoma. In particular, the invention relates to methods for the diagnosis and treatment of early stage melanoma by measuring the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1. Further, the present invention relates to kits comprising one or more reagents and/or devices when used in performing the methods for the diagnosis and treatment of melanoma.

9 Claims, 8 Drawing Sheets

BIOMARKERS OF DISEASE

CROSS-REFERENCE TO RELATED APPLICATIONS

This application is a U.S. National Phase of International Application Serial No. PCT/AU2018/050492 filed on May 22, 2018, which claims priority to Australian Patent Application No. AU 2017901921 filed on May 22, 2017, both of which are hereby incorporated herein by reference for all purposes.

FIELD OF THE INVENTION

The present invention relates generally to methods for the diagnosis and treatment of melanoma.

BACKGROUND OF THE INVENTION

Melanoma is an aggressive form of skin cancer that is responsible for more than 80% of all skin cancer related deaths (Lewis et al., 2005, *American Cancer Society*, 104(4): 1678-1686). Furthermore, the incidence of cutaneous melanoma, the most aggressive and treatment resistant type of skin cancer, continues to increase worldwide (Siegel et al., 2014, *CA: A Cancer Journal for Clinicians*, 64(1): 9-29). It is widely recognised that the early detection of melanoma can significant reduce both morbidity and mortality. Detection of Stage 0 in situ melanoma may result in five-year survival rate as high as 99%. However, this rate plummets to an average of 63% for Stage III disease and an average of 17% for Stage IV disease. Therefore, early detection is central to improving the therapeutic outcomes for patients diagnosed with this aggressive disease.

Currently, the most common method for the diagnosis of melanoma are visual screening methods, such as dermoscopy, reflectance confocal microscopy, total body photography, telederatology and mobile phone applications. Unfortunately, these methods are limited by high subjectivity, observer bias and the ability to identify a visible lesion. Moreover, it is questionable whether these methods are suitable for screening people at higher risk of melanoma, for example, patients with a substantial number of moles (i.e., >100), those with a family history, cases of occult melanoma or those with very thin and unpigmented primary lesions (Loescher et al., 2013, *Seminars in Oncology Nursing*, 29(3): 170-181).

The limitations of visual screening methods are exacerbated by the inefficiencies associated with screening large populations for melanoma, largely due to the time required to screen each individual patient. Furthermore, although Australians are advised to maintain routine annual skin checks, there is little to no capacity for this practice due to a limited number of dermatologists available, especially in rural or remote regions (Chen et al., 2006, *Journal of General Internal Medicine*, 21: 678-682).

The total health care cost for the diagnosis, treatment and management of melanoma is estimated to amount to $30 million annually in Australia (Australian Institute of Health and Welfare, 2010, *Cancer in Australia: an overview*). Previous data has shown that only 5% of these costs are spent on the management of early stage disease, which includes the costs of primary tumour diagnosis and excision, while the remaining 95% is spent on the treatment and management of advanced disease (Durbec et al., 2010, *Archives of Dermatology*, 139(5): 607-612). Therefore, early detection and treatment not only improves patient outcomes, but also significantly reduces the financial burden of disease on the Australian health care system. Complementary diagnostic tools, such as a blood test, are needed to increase melanoma screening efficiency and lower the emphasis on invasive and expensive biopsies (Goldsmith, 2013, *Journal of the American Academy of Dermatology*, 68(3): 517-519). Blood samples are routinely collected as an adjunct to currently utilised diagnostic approaches, therefore, a number of blood-based biomarkers have been proposed for melanoma prognosis, indication of recurrence and assessment of treatment response, including microRNAs (miRNAs) (Stark et al., 2015, *EBioMedicine*, 2(7): 671-680), circulating tumour cells (CTCs) (Freeman et al., 2012, *Journal of Translational Medicine*, 10: 192) and circulating tumour DNA (ctDNA) (Grey et al., 2015, *Oncogene*, 6(39): 42008-42018 and Tsao et al., 2015, *Scientific Reports*, 5(11198): 1-11). However, none of these proposed biomarkers appear to be sufficiently sensitive to detect the initial transformation to malignancy and may not be reliable diagnostic biomarkers for early stage disease.

Autoantibodies that bind to tumour-associated autoantigens can be detected in patient serum months to years prior to the clinical manifestation of a primary tumour (Qiu et al., 2008, *Journal of Clinical Oncology*, 26: 5060-5066; Anderson and LaBaer, 2005, *Journal of Proteome Research*, 4: 1123-1133). This is possibly due to a change in their expression, structural confirmation, and presence of mutations or their release into the surrounding blood serum due to cancer cell lysis (Zaenker et al., 2016, *Autoimmunity Reviews*, 15: 477-483). As a result, autoantibodies have been proposed to be valuable biomarkers for the early detection of many types of cancers, such as prostate, lung, colon, liver and breast cancer (Zaenker and Ziman, 2013, *Cancer Epidemiology, Biomarkers & Prevention*, 22(12): 2161-2181). Autoantibodies have also been suggested to be suitable prognostic markers for melanoma (Sabel et al., 2011, *International Journal of Proteomics*, 1-9; Zörnig et al., 2015, *International Journal of Cancer*, 136: 138-151). However, these studies have not investigated autoantibodies as a marker of early stage disease, nor have they identified a clinically relevant subset of autoantibody biomarkers that can be used to diagnose melanoma with sufficient sensitivity, specificity and predictive value. Accordingly, there remains an urgent need for the identification of autoantibody biomarkers to improve the diagnosis, prognosis and treatment of melanoma.

SUMMARY OF THE INVENTION

In one aspect, the present invention provides a method of determining whether a subject has melanoma, the method comprising:
  a) measuring the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a subject; and
  b) comparing the level of expression of the one or more autoantibodies in the biological sample to a reference value, wherein the reference value is representative of a known or predetermined level of expression of the one or more autoantibodies in a reference sample or a plurality of reference samples from a subject or subjects that have never been diagnosed with cancer, melanoma or an autoimmune disease;

wherein a level of expression of the one or more autoantibodies in the biological sample greater than the reference value provides an indication that the subject has melanoma, and wherein the melanoma is Stage 0, Stage I or Stage II melanoma.

In an embodiment, the step of measuring the expression of one or more autoantibodies in the biological sample comprises measuring the expression of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

The inventor's findings enable a therapeutic regimen, which can be adopted or prescribed, with a view to preventing or delaying the progression of melanoma in a subject. Thus, in another aspect, the present invention provides a method of treating a subject with melanoma, the method comprising the steps of:

a) measuring the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a subject; and b) comparing the level of expression of the one or more autoantibodies in the biological sample to a reference value, wherein the reference value is representative of a known or predetermined level of expression of the one or more autoantibodies in a reference sample or plurality of reference samples from a subject or subjects that have never been diagnosed with cancer, melanoma or an autoimmune disease, wherein a level of expression of the one or more autoantibodies in the biological sample greater than the reference value provides an indication that the subject has melanoma;

c) identifying a subject that has melanoma from step (b); and d) exposing the subject identified in step (c) as having melanoma to a therapeutic regimen for preventing or delaying the progression of melanoma, wherein the melanoma is Stage 0, Stage I or Stage II melanoma.

In an embodiment, the step of measuring the expression of one or more autoantibodies in the biological sample comprises measuring the expression of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

In another aspect of the present invention, there is provided a kit comprising one or more reagents and/or devices for use in performing the method of the present invention, as disclosed herein.

BRIEF DESCRIPTION OF THE FIGURES

Embodiments of the disclosure are described herein, by way of non-limiting example only, with reference to the following drawings.

DETAILED DESCRIPTION OF THE INVENTION

Figure 1:
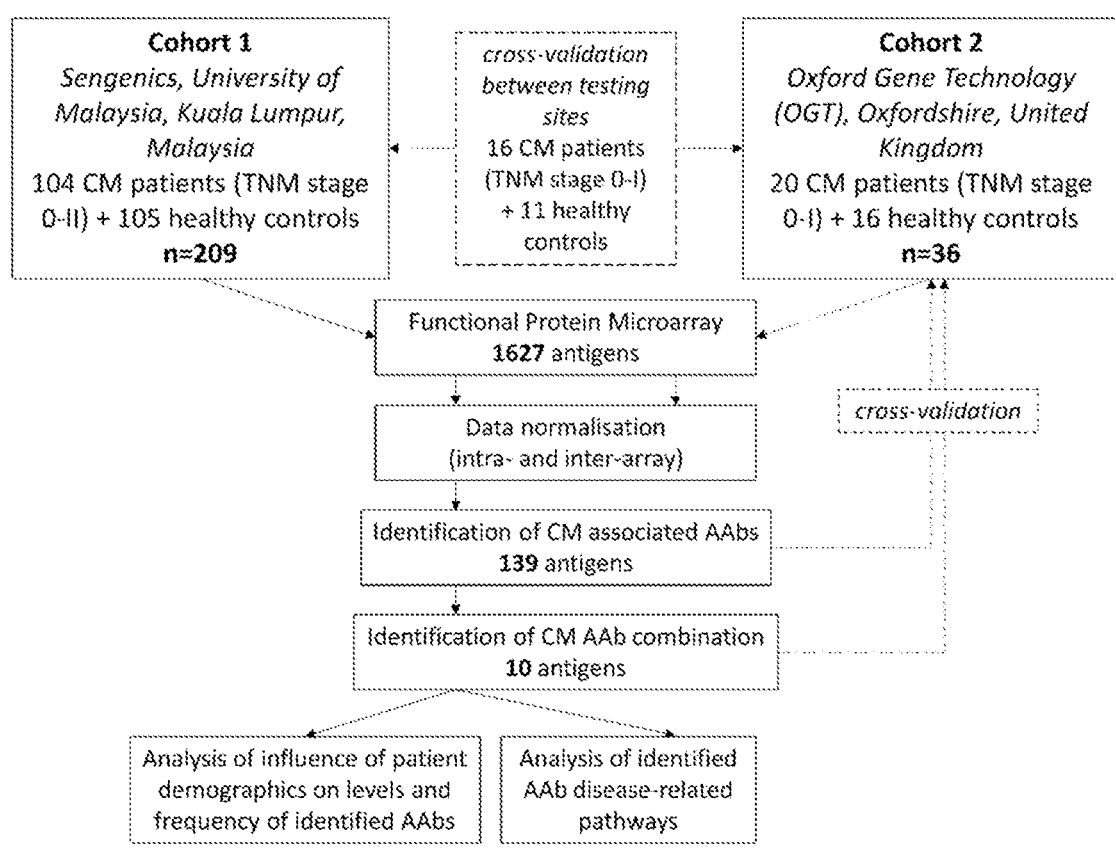
FIG. 1 is a schematic representation of the study design for the identification of diagnostic autoantibodies in melanoma.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an agent" means one agent or more than one agent.

In the context of this specification, the term "about" is understood to refer to a range of numbers that a person of skill in the art would consider equivalent to the recited value in the context of achieving the same function or result.

Methods of Diagnosis

The present invention is predicated, at least in part, on the inventors' surprising finding that the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 can detect melanoma with sufficient sensitivity and specificity to be clinically relevant.

In one aspect of the present invention, there is provided a method of determining whether a subject has melanoma, the method comprising:

a) measuring the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a subject; and b) comparing the level of expression of the one of more autoantibodies in the biological sample to a reference value, wherein the reference value is representative of a known or predetermined level of expression of the one or more autoantibodies in a reference sample or a plurality of reference samples from a subject or subjects that have never been diagnosed with cancer, melanoma or an autoimmune disease;
wherein a level of expression of the one or more autoantibodies in the biological sample greater than the reference value provides an indication that the subject has melanoma, wherein the melanoma is Stage 0, Stage I or Stage II melanoma.

Autoantibodies

"Autoantibodies" or "AAbs" are antibodies produced by the immune system that are directed against one or more of an individual's own proteins. Since tumours originate from autologous cells containing self-antigens, the abnormal exposure or presentation of these "tumour-associated antigens" or "TAAs" facilitates an autoimmune response.

Autoantibodies have become of particular interest as cancer biomarkers as they can be easily extracted from serum via minimally invasive blood collection. Moreover, they exhibit increased levels in very early stages and persist for extended periods after the corresponding antigen is no longer detectable. Importantly, the production of autoantibodies may precede clinical conformation of a tumour by several months or years (Caron et al., 2007, *Molecular Cell Proteomics*, 6(7): 1115-1122).

Increased levels of autoantibodies have been detected in the serum of patients with very early stage cancer (Zayakin et al., 2013, *International Journal of Cancer*, 132: 137-147) and in patients with breast (Anderson et al., 2011, *Journal of Proteome Research*, 10: 85-96), lung (Chapman et al., 2011, *Clinical Cancer Research*, 17(6): 1474-1480), gastrointestinal (Zayakin et al., supra), ovarian (Anderson et al., supra) and prostate (Wang et al., 2005, *New England Journal of Medicine*, 353(12): 1224-1235) cancer. Therefore, although autoantibodies are recognised to be sensitive biomarkers for the detection and surveillance on many types of primary tumours, their diagnostic utility in melanoma is yet to be conclusively demonstrated.

As disclosed herein, the present inventors have shown that the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 have diagnostic capacity with respect to melanoma, including, in an embodiment, the diagnosis of early stage melanoma (i.e., Stage 0, I or II melanoma).

Figure 7:
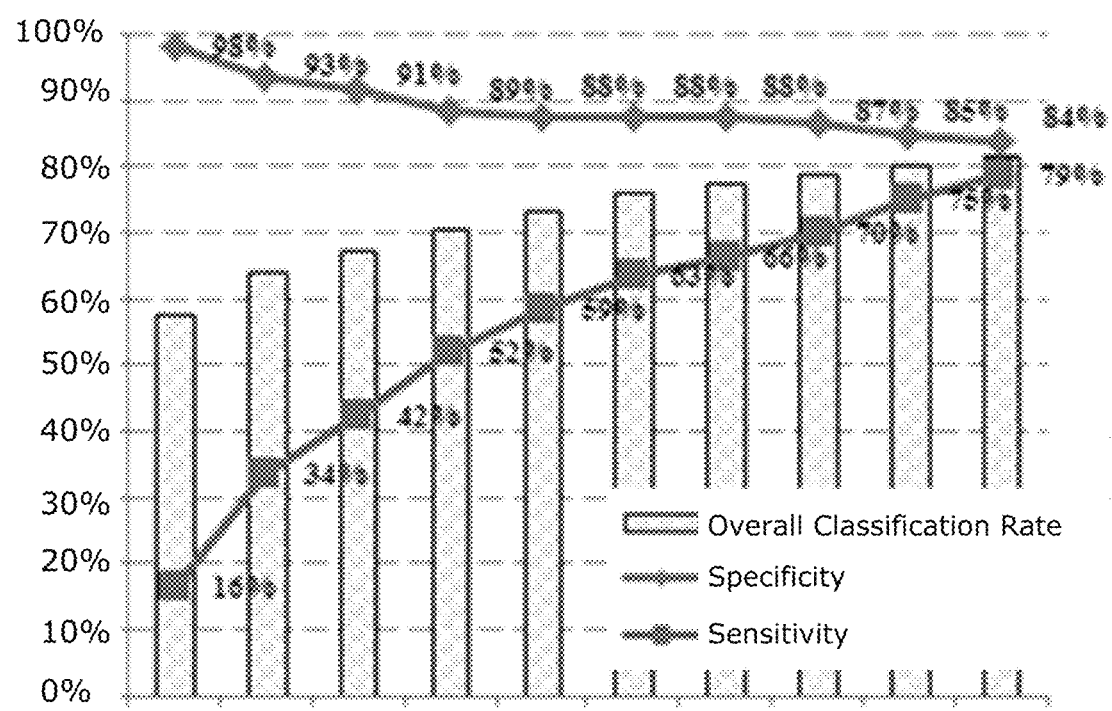
FIG. 7 is a graphical representation of cumulative specificity (blue line), sensitivity (red line) with overall classification rate (%; y-axis) of the 10 autoantibody biomarkers (x-axis).
Figure 8:
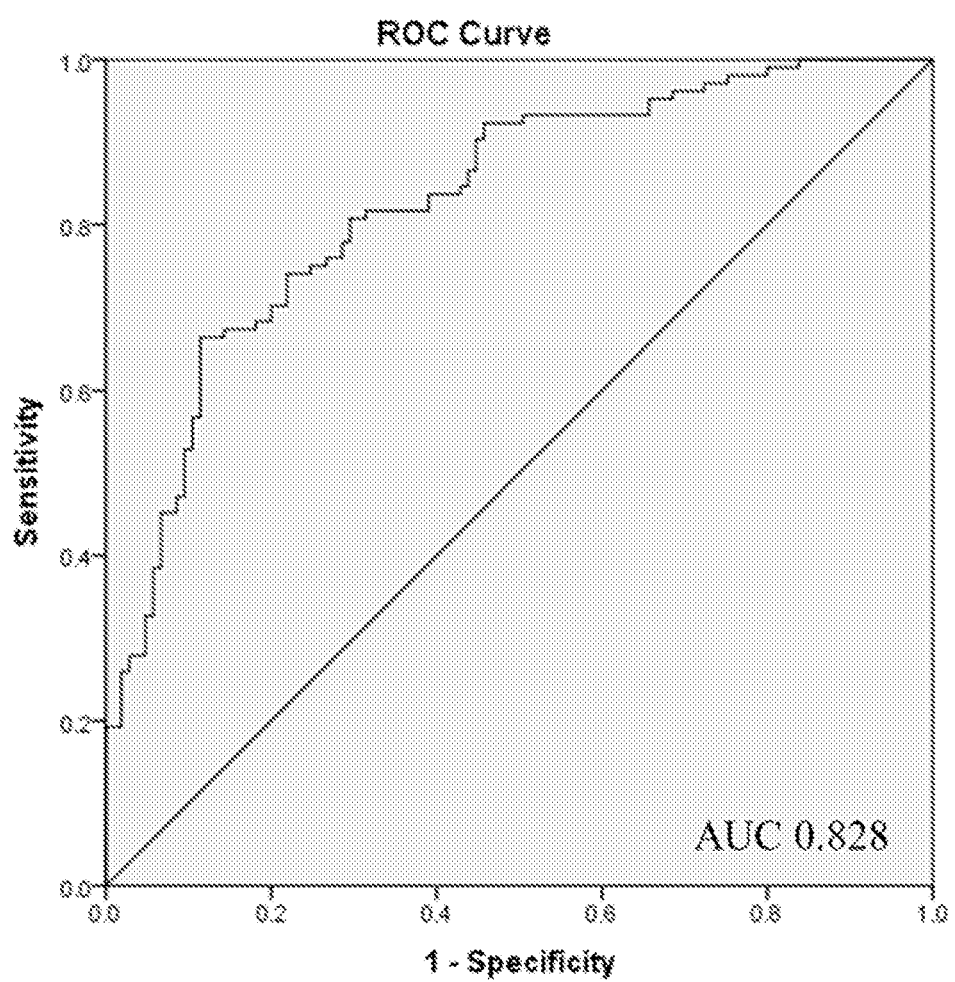
FIG. 8 is a graphical representation of ROC and AUC for individual biomarkers as well as their combination in the discovery cohort.

The present inventors have also shown that the combined expression of the anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 autoantibodies significantly improves the diagnostic capacity for identifying whether or not a subject has melanoma. For instance, the inventors have found that the diagnostic capacity of the expression of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 autoantibodies has a sensitivity of 79% and specificity of 84%, with an AUC of 0.828 for identifying a subject with melanoma as shown in FIGS. 7 and 8 herein.

It is to be understood that the expression of any combination or permutation of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 can be used in accordance with the present invention. In an embodiment, the one or more autoantibodies are anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

The phrase "one or more autoantibodies" is to be understood as meaning at least one autoantibody selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least two autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least three autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least four autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least five autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least six autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least seven autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, at least eight autoantibodies selected from the group consisting of ZBTB7B, PRKCH, TP53, PCTK1, PQBP1, UBE2V1, IRF4, MAPK8_tv2, MSN and TPM1, at least nine autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, or at least ten autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

It is to be understood that, where a combination of two or more autoantibodies is selected and employed in accordance with the present invention, it is desirable that the autoantibodies are selected for combination with the one or more autoantibodies in a combination that will improve, or at least not negate or reduce, the diagnostic capacity of the one or more other autoantibodies. Methods of assessing whether or not one or more autoantibodies improve, or at least do not negate or reduce the capacity of the one or more autoantibodies in a combination to diagnose melanoma, as herein described, would be familiar to persons skilled in the art having regard to the present disclosure.

In an embodiment, the method comprises measuring the expression of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 autoantibodies in a biological sample obtained from a subject.

The term "autoantibody" includes vertebrate autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1, or homologs thereof. Suitable vertebrates that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards, etc.), and fish. In an embodiment, the autoantibodies are human autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

As used herein, the term "autoantibody" also includes homologs thereof. The term "homolog" typically refers to a peptide with similar biological activity, although differs in amino acid sequence at one or more amino acid positions when the sequences are aligned. For example, the amino acid sequences of two homologous autoantibodies may differ by only one amino acid residue within the aligned amino acid sequences. Alternatively, two homologous autoantibodies may differ by two or more amino acid residues when aligned. Homologous autoantibodies may also differ by up to approximately 5%, 10%, 20% or 25% of the amino acid residues when the amino acid sequences of the two homologs are aligned.

Homologs of autoantibodies may be found in the same species (i.e., between two or more individuals of the same species), in related species and/or sub-species, or in different species. For example, for a human autoantibody, homologs include those found in non-human vertebrates and non-vertebrates. Suitable vertebrates that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc), marine mammals (e.g., dolphins, whales), reptiles (snakes, frogs, lizards, etc.), and fish. A preferred homolog is one found in a primate (e.g., a human, ape, monkey, chimpanzee). Alternatively, a laminin chain subunit homolog may be from the same species (e.g., human).

Generally, homologs will have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to a particular amino acid or nucleotide sequence, as determined, for example, by sequence alignment programs known in the art using default parameters (see, e.g., Needleman & Wunsch, 1970). In specific embodiments, the percent identity between nucleotide sequences is determined using the GAP program in the GCG software package, using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5. In some embodiments, the percent identity or similarity between amino acid or nucleotide sequences can be determined using the algorithm of Meyers & Miller (1989) which has been incorporated into the ALIGN program (version 2.0), using a PAM120 weight residue table, a gap length penalty of 12 and a gap penalty of 4.

Measuring the Expression of Autoantibodies

The term "expression" is used herein in its broadest context to denote a measurable presence of the autoantibodies of the present invention, including the production of RNA message (gene expression) or translation of RNA message into proteins or polypeptides (protein expression). For example, the term "autoantibody expression" includes (i) the production of autoantibody RNA message (i.e., autoantibody gene expression), (ii) the translation of autoantibody RNA message into autoantibody protein and/or (iii) the transport of autoantibody protein to the cell surface and into circulation.

In an embodiment, the step of measuring the expression of one or more autoantibodies in the biological sample comprises measuring the protein expression of the one or more autoantibodies in the biological sample.

Suitable methods for measuring autoantibody expression would be known to persons skilled in the art. In some embodiments, it may be desirable to measure the expression of autoantibodies at the protein level. It will be understood that, in some instances, it may be more desirable to measure a gene expression product, such as a transcript (e.g., mRNA) levels, as described elsewhere herein.

Methods of measuring expression products such as proteins and transcripts are known to persons skilled in the art, with illustrative examples described herein. In some embodiments, measuring the expression of autoantibodies comprises determining the level of mRNA encoding the autoantibodies.

As used herein the terms "level" and "amount" are used interchangeably herein to refer to a quantitative amount (e.g., moles or number), a semi-quantitative amount, a relative amount (e.g., weight % or mole % within a class or a ratio), a concentration, and the like. Thus, these terms encompass absolute or relative amounts or concentrations of autoantibodies in a sample, including levels in a population of subjects represented as mean levels and standard deviations, as shown in some of the Figures herein.

Autoantibodies may be quantified or detected using any suitable technique, including, but not limited to, nucleic acid- and protein-based assays. In illustrative nucleic acid-based assays, nucleic acid is isolated from cells contained in a biological sample according to standard methodologies (Sambrook, et al., 1989, *Molecular Cloning: A Laboratory Manual*; and Ausubel et al., 1994, *Current Protocols in Molecular Biology*). The nucleic acid is typically fractionated (e.g., poly A$^+$ RNA) or whole cell RNA. Where RNA is used as the subject of detection, it may be desired to convert the RNA to a complementary DNA. In some embodiments, the nucleic acid is amplified by a template-dependent nucleic acid amplification technique. A number of template dependent processes are available to amplify the autoantibody-encoding nucleotide sequences present in a given sample. An exemplary nucleic acid amplification technique is the polymerase chain reaction (referred to as PCR), which is described in detail in U.S. Pat. Nos. 4,683,195, 4,683,202 and 4,800,159, Ausubel et al. (supra), and in Innis et al., (1990). Briefly, in PCR, two primer sequences are prepared that are complementary to regions on opposite complementary strands of the autoantibody nucleotide sequence. An excess of deoxynucleotide triphosphates are added to a reaction mixture along with a DNA polymerase, e.g., Taq polymerase. If a cognate autoantibody nucleotide sequence is present in a sample, the primers will bind to the sequence and the polymerase will cause the primers to be extended along the sequence by adding on nucleotides. By raising and lowering the temperature of the reaction mixture, the extended primers will dissociate from the autoantibody nucleotide sequence to form reaction products, excess primers will bind to the autoantibody nucleotide sequence and to the reaction products and the process is repeated. A reverse transcriptase PCR amplification procedure may be performed in order to quantify the amount of mRNA amplified. Methods of reverse transcribing RNA into cDNA are well known and described in Sambrook et al., 1989, supra. Alternative methods for reverse transcription utilize thermostable, RNA-dependent DNA polymerases. These methods are described in WO 90/07641. Polymerase chain reaction methodologies are well known in the art.

In an embodiment, the template-dependent amplification involves quantification of transcripts in real-time. For example, RNA or DNA may be quantified using the Real-Time PCR technique (Higuchi et al., 1992, *Biotechnology*, 11(9): 1026-1030). By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR products and the relative mRNA abundance is only true in the linear range of the PCR reaction. The final concentration of the target DNA in the plateau portion of the curve is determined by the availability of reagents in the reaction mix and is independent of the original concentration of target DNA. In specific embodiments, multiplexed, tandem PCR (MT-PCR) is employed, which uses a two-step process for gene expression profiling from small quantities of RNA or DNA, as described for example in US Pat. Appl. Pub. No. 20070190540. In the first step, RNA is converted into cDNA and amplified using multiplexed gene specific primers. In the second step each individual gene is quantitated by real time PCR.

In some embodiments, autoantibody nucleic acids are quantified using blotting techniques, which are well known to those of skill in the art. Southern blotting involves the use of DNA as a target, whereas Northern blotting involves the use of RNA as a target. Each provides different types of information, although cDNA blotting is analogous, in many aspects, to blotting or RNA species. Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter. Subsequently, the blotted target is incubated with a probe (usually labelled) under conditions that promote denaturation and re-hybridisation. Because the probe is designed to base pair with the target, the probe will bind a portion of the target sequence under renaturing conditions. Unbound probe is then removed, and detection is accomplished as described above. Following detection/quantification, one may compare the results seen in a given subject with a control reaction or a statistically significant reference group or population of control subjects as defined herein. In this way, it is possible to correlate the amount of a biomarker nucleic acid detected with the likelihood that a subject has melanoma.

Also contemplated herein are biochip-based technologies such as those described by Hacia et al. (1996) and Shoemaker et al. (1996). Briefly, these techniques involve quantitative methods for analysing large numbers of genes rapidly and accurately. By tagging genes with oligonucleotides or using fixed probe arrays, one can employ biochip technology to segregate target molecules as high-density arrays and screen these molecules on the basis of hybridization. See also Pease et al. (1994); Fodor et al. (1991). Briefly, nucleic acid probes to autoantibody nucleotide sequences are made and attached to biochips to be used in screening and diagnostic methods, as outlined herein. The nucleic acid probes attached to the biochip are designed to be substantially complementary to specific expressed autoantibody nucleotide sequences, i.e., the target sequence (either the target sequence of the sample or to other probe sequences, for example in sandwich assays), such that hybridization of the target sequence and the probes of the present invention occur. This complementarity need not be perfect; there may be any number of base pair mismatches, which will interfere with hybridization between the target sequence and the nucleic acid probes of the present invention. However, if the number of mismatches is so great that no hybridization can occur under even the least stringent of hybridization conditions, the sequence is not a complementary target sequence. In certain embodiments, more than one probe per sequence is used, with either overlapping probes or probes to different sections of the target being used. That is, two, three, four or more probes, with three being desirable, are used to build in a redundancy for a particular target. The probes can be overlapping (i.e. have some sequence in common), or separate.

In an illustrative biochip analysis, oligonucleotide probes on the biochip are exposed to or contacted with a nucleic acid sample suspected of containing one or more biomarker polynucleotides under conditions favouring specific hybridization. Sample extracts of DNA or RNA, either single or double-stranded, may be prepared from fluid suspensions of biological materials, or by grinding biological materials, or following a cell lysis step which includes, but is not limited to, lysis effected by treatment with SDS (or other detergents), osmotic shock, guanidinium isothiocyanate and lysozyme. Suitable DNA, which may be used in the method of the invention, includes cDNA. Such DNA may be prepared by any one of a number of commonly used protocols as for example described in Ausubel, et al., supra, and Sambrook, et al., supra.

Suitable RNA, which may be used in the method of the invention, includes messenger RNA, complementary RNA transcribed from DNA (cRNA) or genomic or subgenomic RNA. Such RNA may be prepared using standard protocols as for example described in the relevant sections of Ausubel, et al., supra and Sambrook, et al., supra).

cDNA may be fragmented, for example, by sonication or by treatment with restriction endonucleases. Suitably, cDNA is fragmented such that resultant DNA fragments are of a length greater than the length of the immobilized oligonucleotide probe(s) but small enough to allow rapid access thereto under suitable hybridization conditions. Alternatively, fragments of cDNA may be selected and amplified using a suitable nucleotide amplification technique, as described for example above, involving appropriate random or specific primers.

Usually the target biomarker polynucleotides are detectably labelled so that their hybridization to individual probes can be determined. The target polynucleotides are typically detectably labelled with a reporter molecule illustrative examples of which include chromogens, catalysts, enzymes, fluorochromes, chemiluminescent molecules, bioluminescent molecules, lanthanide ions (e.g., $Eu^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like. Illustrative labels of this type include large colloids, for example, metal colloids such as those from gold, selenium, silver, tin and titanium oxide. In some embodiments, in which an enzyme is used as a direct visual label, biotinylated bases are incorporated into a target polynucleotide.

The hybrid-forming step can be performed under suitable conditions for hybridizing oligonucleotide probes to test nucleic acid including DNA or RNA. In this regard, reference may be made, for example, to "Nucleic Acid Hybridization, A Practical Approach (Homes & Higgins, 1985). In general, whether hybridization takes place is influenced by the length of the oligonucleotide probe and the polynucleotide sequence under test, the pH, the temperature, the concentration of mono- and divalent cations, the proportion of G and C nucleotides in the hybrid-forming region, the viscosity of the medium and the possible presence of denaturants. Such variables also influence the time required for hybridization. The preferred conditions will therefore depend upon the particular application. Such empirical conditions, however, can be routinely determined without undue experimentation.

After the hybrid-forming step, the probes are washed to remove any unbound nucleic acid with a hybridization buffer. This washing step leaves only bound target polynucleotides. The probes are then examined to identify which probes have hybridized to a target polynucleotide. The hybridization reactions are then detected to determine which of the probes has hybridized to a corresponding target sequence. Depending on the nature of the reporter molecule associated with a target polynucleotide, a signal may be instrumentally detected by irradiating a fluorescent label with light and detecting fluorescence in a fluorimeter; by providing for an enzyme system to produce a dye which could be detected using a spectrophotometer; or detection of a dye particle or a coloured colloidal metallic or non metallic particle using a reflectometer; in the case of using a radioactive label or chemiluminescent molecule employing a radiation counter or autoradiography. Accordingly, a detection means may be adapted to detect or scan light associated with the label which light may include fluorescent, luminescent, focused beam or laser light. In such a case, a charge couple device (CCD) or a photocell can be used to scan for emission of light from a probe: target polynucleotide hybrid from each location in the micro-array and record the data directly in a digital computer. In some cases, electronic detection of the signal may not be necessary. For example, with enzymatically generated colour spots associated with nucleic acid array format, visual examination of the array will allow interpretation of the pattern on the array. In the case of a nucleic acid array, the detection means is suitably interfaced with pattern recognition software to convert the pattern of signals from the array into a plain language genetic profile. In certain embodiments, oligonucleotide probes specific for different biomarker polynucleotides are in the form of a nucleic acid array and detection of a signal generated from a reporter molecule on the array is performed using a 'chip reader'. A detection system that can be used by a 'chip reader' is described for example by Pirrung et al (U.S. Pat. No. 5,143,854). The chip reader will typically also incorporate some signal processing to determine whether the signal at a particular array position or feature is a true positive or maybe a spurious signal. Exemplary chip readers are described for example by Fodor et al (U.S. Pat. No. 5,925,525). Alternatively, when the array is made using a mixture of individually addressable kinds of labelled microbeads, the reaction may be detected using flow cytometry.

In other illustrative embodiments, autoantibody protein levels can be measured using protein-based assays known in the art. For example, an antibody-based technique may be employed to determine the level of an autoantibody in a sample, non-limiting examples of which include immunoassays, such as the enzyme-linked immunosorbent assay (ELISA), immunohistochemistry (IHC) and the radioimmunoassay (RIA).

In an embodiment, protein expression is measured using a multiplexed protein expression analysis method. In another embodiment, the multiplexed protein expression analysis method is a protein microarray or Luminex bead array.

Protein-capture arrays that permit simultaneous detection and/or quantification of a large number of proteins may also be employed. For example, low-density protein arrays on filter membranes, such as the universal protein array system (Ge, 2000) allow imaging of arrayed antigens using standard ELISA techniques and a scanning charge-coupled device (CCD) detector. Immuno-sensor arrays have also been developed that enable the simultaneous detection of clinical analytes. It is now possible using protein arrays, to profile protein expression in bodily fluids, such as in serum of healthy or diseased subjects. Exemplary protein capture arrays include protein function arrays comprising spatially addressed protein-binding molecules (i.e., antigens), which can facilitate extensive parallel analysis of autoantibodies with specificity for the antigens that comprise the protein function array. Central to this type of analysis is the retention of the correctly folded protein confirmation of the arrayed antigen. Protein function arrays have been shown to have the required properties of specificity and acceptable background, and are available commercially (e.g., Sengenics). Various methods for the preparation of protein function arrays have been reported (see, e.g., Gnjatic et al., 2009, *Journal of Immunological Methods,* 341(50): 1-2; PCT/GB01/00395, PCT/GB02/05499, PCT/GB03/00362). Individual spatially distinct functional proteins are typically attached to a support surface, which is generally planar or contoured. Common physical supports include glass slides, silicon, microwells, nitrocellulose or PVDF membranes, and magnetic and other microbeads.

Particles in suspension can also be used as the basis of arrays, providing they are coded for identification; systems include colour coding for microbeads (e.g., available from Luminex, Bio-Rad and Nanomics Biosystems) and semiconductor nanocrystals (e.g., QDots™, available from Quantum Dots), and barcoding for beads (UltraPlex™, available from Smartbeads) and multimetal microrods (Nanobarcodes™ particles, available from Surromed). Beads can also be assembled into planar arrays on semiconductor chips (e.g., available from LEAPS technology and BioArray Solutions). Where particles are used, individual protein-capture agents (e.g., anti-autoantibody antibodies or autoantibody-binding fragments thereof) are typically attached to an individual particle to provide the spatial definition or separation of the array. The particles may then be assayed separately, but in parallel, in a compartmentalized way, for example in the wells of a microtiter plate or in separate test tubes.

In an illustrative example, a patient or control serum sample is delivered to a protein function array under conditions suitable for protein or peptide binding, and the array is washed to remove unbound or non-specifically bound components of the sample from the array. Next, the array is incubated with fluorescently-labelled antibody to detect the interaction between array antigens and serum autoantibodies. The presence or amount of protein or peptide bound to each feature of the array is detected using a suitable fluorescence detection system. The amount of protein bound to a feature of the array is proportional to the intensity of fluorescence. In certain embodiments, local background fluorescence obtained from control features of the array are automatically subtracted and relative fluorescent units (rfu) for each feature of the array is recorded.

In some embodiments, the protein function array is Immunome Protein Array (Sengenics).

Another illustrative example of a protein-capture array is a Luminex-based multiplex assay, which is a bead-based multiplexing assay, where beads are internally dyed with fluorescent dyes to produce a specific spectral address. Biomolecules (such as an oligo or antibody) can be conjugated to the surface of beads to capture analytes of interest; that is, autoantibodies or a nucleic acid molecule encoding same. Flow cytometric or other suitable imaging technologies known to persons skilled in the art can then be used for characterization of the beads, as well as for detection of analyte presence. The Luminex technology enables are large number of proteins, genes or other gene expression products (e.g., 100 or more, 200 or more, 300 or more, 400 or more) to be detected using very small sample volume (e.g., in a 96 or 384-well plate).

In some embodiments, the expression of the autoantibodies can be normalised against a housekeeping biomarker. The term "housekeeping biomarker" refers to a biomarker or group of biomarkers (e.g., polynucleotides and/or polypeptides), which are typically found at a constant level in the cell type(s) or tissue(s) being analysed and across the conditions being assessed. In some embodiments, the housekeeping biomarker is a "housekeeping gene." A "housekeeping gene" refers herein to a gene or group of genes which encode proteins whose activities are essential for the maintenance of cell function and which are typically found at a constant level in the cell type(s) being analysed and across the conditions being assessed.

In other embodiments, the expression of the autoantibodies measured using a protein array can be normalised by both intra- and inter-array data normalisation. For example, the overall median value of all median relative fluorescent units (rfu) of each protein in a protein function array (excluding data from control proteins) is calculated and intra-array normalisation achieved by dividing the median of the quadruplicate spots of each protein on the array, by the overall median value of all the proteins on the array in each sample. Inter-array normalisation can be achieved using bioinformatics software packages that are known in the art. For example, inter-array normalisation can be achieved using the normalize.quantiles package in R (Bolstad et al., 2003, *Bioinformatics*, 19(2): 185-193).

It would be understood by those skilled in the art, as described elsewhere herein, that the method of analysing the expression of autoantibodies in a biological sample can be quantitative, semi-quantitative or qualitative in nature. For example, quantitative analyses will typically provide a concentration or number of an autoantibody nucleic acid molecule or protein in the sample within an appropriate error margin (e.g., mean+/−standard deviation). By contrast, semi-quantitative or qualitative analyses will typically provide an indication of the relative amount of an autoantibody in a sample. This may involve a comparison of an amount of an autoantibody protein in a first sample with an amount of an autoantibody protein in a second sample and making a determination as to the relative amount of the autoantibody protein between the first and second samples.

It will be understood by persons skilled in the art that, where a comparison is made to a reference value, then the manner in which the biological sample is assessed for the expression of the one or more autoantibodies should be substantially identical to the manner in which the reference value is derived in order to ensure that an appropriate comparison can be made for the purposes of determining whether or not a subject has melanoma.

In an embodiment, the methods disclosed herein comprise measuring the protein expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in the biological sample by quantitative or semi-quantitative protein analysis methods, either as individual biomarkers or as a multiplexed biomarker panel. These methods will be known to persons skilled in the art, an illustrative example of which is disclosed elsewhere herein.

In an embodiment, the step of measuring the expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in the biological sample comprises measuring the protein expression of the one or more autoantibodies in the biological sample.

In another embodiment, the step of measuring the expression of the one or more autoantibodies comprises measuring the protein expression of each of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in the biological sample.

Melanoma

Melanoma is a malignant tumour of melanocytes, which are the cells that produce the pigment melanin and are derived from the neural crest. Although the majority of melanomas arise in the skin, they may also arise from mucosal surfaces or at other sites to which neural cells migrate, including the uveal tract. Malignant melanoma accounts for the largest number of deaths attributed to skin cancer and is predicted to be the eighth most common cause of cancer death in Australia in 2017 (Australian Institute of Health and Welfare, 2017, *Cancer in Australia*).

The term "melanoma" includes melanoma, metastatic melanoma, melanomas derived from melanocytes or nevus cells, superficial spreading melanoma, nodular melanoma, lentigo maligna melanoma, acral lentiginous melanoma, demoplastic melanoma, ocular melanoma (i.e., uveal and conjunctival), polyploid melanoma, naevoid melanoma and anorectal melanoma).

Melanoma is commonly diagnosed by visual screening methods, such as dermoscopy, reflectance confocal microscopy, total body photography, telederatology and mobile phone applications. Thereafter, histological conformation of the diagnosis is performed by taking an excision biopsy and, in some cases, a sentinel lymph node biopsy. If melanoma is found in a tissue sample, an assessment will usually be undertaken to determine the stage, or extent, of the disease, with respect to the size and spread of the melanoma. The TNM system is often employed for this purpose, where (T) denotes the size of the melanoma, (N) denotes the spread of the melanoma to the lymph nodes and (M) denotes the spread of melanoma cells to different parts of the body.

Once the TNM is determined, a stage of 0, I, II, III or IV is assigned to the melanoma. Stage 0 is the earliest stage of melanoma and limited to in situ tumours that are confined to the cells in the epidermis with no detectable cancer cells in the dermis. Stage I melanoma can be defined in two ways: 2 mm in thickness without ulceration or detectable cancer cells in the regional lymph nodes or metastases at distant sites; or up to 1 mm in thickness with ulceration but no detectable cancer cells in the regional lymph nodes or metastases at distant sites. Stage II tumours are classified into three distinct sub-stages, stage IIA have a primary tumour that ranges from 1 mm but not more than 4 mm in thickness with ulceration but no detectable cancer cells in the regional lymph nodes or metastases at distant sites; stage IIB have a primary tumour that ranges from 2.01 mm to >4 mm in thickness with ulceration but no detectable cancer cells in the regional lymph nodes or metastases at distant sites; and stage IIC have a primary tumour >4 mm in thickness with ulceration but no detectable cancer cells in the regional lymph nodes or metastases at distant sites. Stage III tumours are classified into three distinct sub-stages, with primary tumours of any thickness and cancer cells present to a various extent in regional lymph nodes but no metastases at distinct sites. Finally, Stage IV tumours represent the most advanced stage of disease and are characterised by a primary tumour of any thickness with metastases present in regional lymph nodes and distant sites.

In an embodiment, the present invention is particularly adapted for the diagnosis of a Stage 0, I or II melanoma.

Until the present invention, there has been no reliable diagnostic test available that can identify whether a patient has melanoma using blood- or serum-based biomarkers. This is particularly the case for early stage melanomas, where detection may result in significantly improved patient prognosis.

The inventors have surprisingly shown that the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 can be used to diagnose melanoma, and in particular, early stage melanoma.

Subject

The terms "subject," "individual" and "patient" are used interchangeably herein to refer to any subject to which the present disclosure may be applicable, particularly a vertebrate subject, and even more particularly a mammalian subject. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards, etc.), and fish. In some embodiments, the subject is a primate (e.g., a human, ape, monkey, chimpanzee). In a preferred embodiment, the subject is a human.

Biological Sample

The biological sample can be any sample in which changes in the expression of autoantibodies reflect the risk of melanoma. Suitable biological samples could be determined by persons skilled in the art. For example, the level of expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a first subject who undergoing screening to detect melanoma can be compared to a level of expression of the one or more autoantibodies in a biological sample obtained from substantially the same anatomical region of a second subject who is free of melanoma and/or has had no history of melanoma, wherein a higher level of expression of the one or more antibodies in the biological sample from the first subject as compared to the level of expression in the biological sample from the second subject is indicative that the first subject has melanoma, in accordance with the method of the present invention.

A biological sample may include a sample that has been obtained, extracted, untreated, treated, diluted or concentrated from a subject. In some embodiments, the biological sample has not been extracted from the subject, particularly where the determination steps in accordance with the present invention (e.g., the expression of the panel of autoantibodies) can be performed in situ.

Non-limiting examples of suitable biological samples include, but are not limited to, tissue, such as a biopsy sample or a resected tumour, bodily fluid (for example, blood, serum, plasma, saliva, urine, tears, peritoneal fluid, ascetic fluid, vaginal secretion, breast fluid, breast milk, lymph fluid, cerebrospinal fluid or mucosa secretion), umbilical cord blood, chorionic villi, amniotic fluid, an embryo, embryonic tissues, lymph fluid, cerebrospinal fluid, mucosa secretion, or other body exudate, fecal matter and one or more cells or extracts thereof that express laminin chain subunits (nucleic acid or protein), including subcellular structures obtained using protocols well established within the art.

In an embodiment, the biological sample comprises blood or a component of blood, such as peripheral blood, or a fraction or extract thereof. The biological sample may comprise blood cells, such as mature, immature or developing leukocytes, including lymphocytes, polymorphonuclear leukocytes, neutrophils, monocytes, reticulocytes, basophils, coelomocytes, eosinophils, megakaryocytes, macrophages, dendritic cells, natural killer cells, or fraction of such cells (e.g., a nucleic acid or protein fraction).

In an embodiment disclosed herein, the component of blood is serum. In another embodiment, the component of blood is plasma.

The biological sample may be processed and analysed for the purpose of determining the expression of the one or more autoantibodies, in accordance with the present invention, almost immediately following collection (i.e., as a fresh sample), or it may be stored for subsequent analysis. If storage of the biological sample is desired or required, it would be understood by persons skilled in the art that it should ideally be stored under conditions that preserve the integrity of the biomarker of interest within the sample (e.g., at −80° C.).

The terms "obtain", "obtaining", "obtained" and the like, as used herein, are meant to come into possession. Biological or reference samples so obtained include, for example, nucleic acid extracts or polypeptide extracts isolated or derived from a particular source. For instance, the extract may be isolated directly from a biological tissue of the subject.

Reference Value

The methods disclosed herein comprise a comparison step (i.e., to identify whether the subject has melanoma) in which the expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in the biological sample of the test subject is compared to the expression of the one or more autoantibodies in a reference sample or a plurality of reference samples that is measured prior to, concurrently or subsequent to the expression of the one or autoantibodies in the biological sample from the test subject, wherein the reference sample or plurality of reference samples is obtained from a different subject or subjects who have never been diagnosed with cancer, melanoma or an autoimmune disease. It is to be understood, however, that the comparison step (i.e., to identify whether the subject has melanoma) does not need to rely upon a comparison with a level of expression of the one or more autoantibodies in the biological sample to the level of expression in reference sample. For example, the comparison may be carried out using a reference value; that is, a known or predetermined level of expression of the one or more autoantibodies that is associated with the absence of melanoma, as described elsewhere herein.

The term "reference value" is referred to interchangeably herein as a "control value". In an illustrative example, the comparison may be carried out using a reference value that is representative of a known or predetermined level of expression of the one or more autoantibodies in a reference sample or a plurality of reference samples, which is associated with the absence of melanoma, as described elsewhere herein. The term "reference sample" is also referred to herein as a "control sample".

The reference value is typically a predetermined level of expression of the one or more autoantibodies that is representative of the level of expression in a particular cohort or population of subjects (e.g., normal healthy subjects, subjects that have never been diagnosed with melanoma, any other type of cancer or any autoimmune diseases, etc.). The reference value may be represented as an absolute number, or as a mean value (e.g., mean+/−standard deviation), such as when the reference value is derived from (i.e., representative of) a population of individuals.

The reference value may be equal to or not significantly different from the level of expression of the one or more autoantibodies in a sample population representative of patients who have never been diagnosed with cancer, melanoma or an autoimmune disease. Thus, a level of expression of the one or more autoantibodies in a biological sample from a test subject that is greater than the reference value is indicative of melanoma in the test subject. Conversely, a level of expression of the one or more autoantibodies in a biological sample from a test subject that is equal to or less than the reference value indicates that the test subject does not have melanoma.

Whilst persons skilled in the art would understand that using a reference value that is derived from a plurality of reference samples is likely to provide a more accurate representation of the level of expression in that particular population (e.g., for the purposes of the methods and protocols disclosed herein), in some embodiments, the reference value can be a level of expression of the one or more autoantibodies in a single reference sample.

In an embodiment, the reference value is representative of a level of expression of the one or more autoantibodies in a reference sample or a plurality of reference samples of a healthy subject or subjects, wherein the term "healthy subject" is defined as a subject that has never been diagnosed with cancer, melanoma or an autoimmune disease, wherein a level of expression of the one or more autoantibodies in the biological sample greater than the reference value is indicative that the subject has melanoma.

In an embodiment, the reference value is representative of a level of expression of the one or more autoantibodies in a reference sample or a plurality of reference samples of a healthy subject or subjects that have never been diagnosed with cancer, melanoma or an autoimmune disease, wherein a level of expression of the one or more autoantibodies in the biological sample less than or equal to the reference value is indicative that the subject does not have melanoma.

In an embodiment, the reference value is representative of a level of expression of the one or more autoantibodies in a biological sample of a subject or subjects that have never been diagnosed with cancer, melanoma or an autoimmune disease, wherein the level of expression of the one or more autoantibodies in the biological sample is greater than the reference value and is indicative of early stage melanoma, wherein "early stage melanoma" means Stage 0, I or II melanoma.

For any particular autoantibody, a distribution of autoantibody expression levels for subjects who have or do not have melanoma may overlap. Under such conditions, a test may not absolutely distinguish a subject who has melanoma from a subject who does not have melanoma with absolute (i.e., 100%) accuracy, and the area of overlap indicates where the test cannot distinguish the two subjects. Accordingly, in an embodiment the reference value can be selected, above which (or below which, depending on how the expression of one or more autoantibodies changes during melanoma progression) the test is considered to be "positive" and below which the test is considered to be "negative." The area under the receiver operating characteristic (ROC) curve (AUC) provides the C-statistic, which is a measure of the probability that the perceived measurement will allow correct identification of a condition (see, e.g., Hanley et al., 1982, *Radiology*, 143(1): 29-36).

In some embodiments, AUC or ROC values are used as a measure of a method's ability to detect melanoma. The term "area under the curve" or "AUC" refers to the area under the curve of a ROC curve, both of which are well known in the art. AUC measures are useful for comparing the accuracy of a classifier across the complete data range. Classifiers with a greater AUC have a greater capacity to classify unknowns correctly between two groups of interest (e.g., a healthy subject group and a melanoma group). ROC curves are useful for plotting the performance of a particular feature (e.g., any of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 and/or any item of additional biomedical information) in distinguishing or discriminating between two populations (e.g., cases having melanoma and control healthy subjects). Typically, the feature data across the entire population (e.g., the cases and controls) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to produce a single value, and this single value can be plotted in a ROC curve. Additionally, any combination of multiple features, in which the combination derives a single output value, can be plotted in a ROC curve. These combinations of features may comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one. An AUC ROC value may be thought of as equivalent to the Mann-Whitney U test, which tests for the median difference between scores obtained in the two groups considered if the groups are of continuous data, or to the Wilcoxon test of ranks.

In an embodiment, the reference value is determined by reference to the AUC ROC values relating to the expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1.

In some embodiments, the expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 is selected to discriminate between subjects with or without melanoma with at least about 50%, 55% 60%, 65%, 70%, 75%, 80%, 85%, 90%, 95% accuracy or having a C-statistic of at least about 0.50, 0.55, 0.60, 0.65, 0.70, 0.75, 0.80, 0.85, 0.90, 0.95.

In the case of a positive likelihood ratio, a value of 1 indicates that a positive result is equally likely among subjects in both the "melanoma" and "healthy subject" groups; a value greater than 1 indicates that a positive result is more likely in the melanoma group; and a value less than 1 indicates that a positive result is more likely in the healthy subject group. In this context, "melanoma group" is meant to refer to a population of reference individuals considered to melanoma and a "healthy subject" is meant to refer to a group of subjects that have never been diagnosed with cancer, melanoma or an autoimmune disease. In the case of a negative likelihood ratio, a value of 1 indicates that a negative result is equally likely among subjects in both the "melanoma" and "healthy subject" groups; a value greater than 1 indicates that a negative result is more likely in the "melanoma" group; and a value less than 1 indicates that a negative result is more likely in the "healthy subject" group. In the case of an odds ratio, a value of 1 indicates that a positive result is equally likely among subjects in both the "melanoma" and "healthy subject" groups; a value greater than 1 indicates that a positive result is more likely in the "melanoma" group; and a value less than 1 indicates that a positive result is more likely in the "healthy subject" group. In the case of an AUC ROC value, this is computed by numerical integration of the ROC curve. The range of this value can be 0.5 to 1.0. A value of 0.5 indicates that a classifier (e.g., an autoantibody expression profile) is no better than a 50% chance to classify unknowns correctly between two groups of interest, while 1.0 indicates the relatively best diagnostic accuracy. In certain embodiments, autoantibodies and/or autoantibody panels are selected to exhibit a positive or negative likelihood ratio of at least about 1.5 or more or about 0.67 or less, at least about 2 or more or about 0.5 or less, at least about 5 or more or about 0.2 or less, at least about 10 or more or about 0.1 or less, or at least about 20 or more or about 0.05 or less.

In certain embodiments, the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 are selected to exhibit an AUC ROC value of greater than 0.5, preferably at least 0.6, more preferably 0.7, still more preferably at least 0.8, even more preferably at least 0.9, and most preferably at least 0.95.

Therapeutic Regimen

A subject who is identified as having melanoma can be stratified into a treatment group where an appropriate therapeutic regimen can be adopted or prescribed with a view to treating or preventing melanoma and/or melanoma progression. Conversely, subjects identified as having early stage melanoma can be spared an otherwise taxing therapeutic regimen or, alternatively, a less aggressive therapeutic regimen (e.g., a lower dose of chemotherapeutic agent or radiation dose) can be adopted or prescribed. Thus, in an embodiment, the methods disclosed herein further comprise the step of exposing (i.e., subjecting) the subject identified as having melanoma to a therapeutic regimen for treating the melanoma and/or melanoma progression, including a therapeutic regimen for preventing or delaying melanoma progression.

In an embodiment, the therapeutic regimen comprises surgery and the administration of a chemotherapeutic agent, radiotherapy, immunotherapy and/or targeted molecular therapy.

In another aspect disclosed herein, there is provided a method of treating a subject with melanoma, the method comprising the steps of:
  a) measuring the expression of one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a subject;
  b) comparing the level of expression of the one or more autoantibodies in the biological sample to a reference value, wherein the reference value is representative of a level of expression of the one or more autoantibodies in a reference sample or a plurality of reference samples from a subject or subjects that have never been diagnosed with cancer, melanoma or an autoimmune disease, wherein a level of expression of the one or more autoantibodies in the biological sample greater than the reference value provides an indication that the subject has melanoma;
  c) identifying a subject that has melanoma from step (b); and
  d) exposing the subject identified in step (c) as having melanoma to a therapeutic regimen for preventing or delaying the progression of the melanoma, wherein the melanoma is Stage 0, Stage I or Stage II melanoma.

Suitable therapeutic regimens will be familiar to persons skilled in the art, the choice of which is likely to be determined by factors such as, but not limited to, the type of melanoma (e.g., superficial spreading melanoma, nodular melanoma, lentigo maligna melanoma, acral lentiginous melanoma, demoplastic melanoma, ocular melanoma (i.e., uveal and conjunctival), polyploid melanoma, naevoid melanoma and anorectal melanoma), the severity of the melanoma (e.g., stage of progression), the age and general health status of the patient, etc. In an embodiment, the method the therapeutic regimen comprises surgery, optionally followed by the administration of a chemotherapeutic agent, radiotherapy, immunotherapy and/or targeted molecular therapy. Where melanoma is detected by blood test, the therapeutic regimen will further comprise the identification of the primary lesion by a skin check prior to surgical removal of the primary lesion, optionally followed by the administration of a chemotherapeutic agent, radiotherapy, immunotherapy and/or target therapy.

Suitable chemotherapeutic agents will be known to persons skilled in the art. Illustrative examples of suitable chemotherapeutic agents include dacarbazine, temozolomide, nab-paclitaxel, paclitaxel, cisplatin, carboplatin and vinblastine.

Radiation therapy (also referred to as radiotherapy) uses high-energy electromagnetic radiation to damage cancer cells and stop them from proliferating. When used, it is generally in combination with surgery and chemotherapy, or used only with chemotherapy in cases where the individual is unable to undergo resection. Radiation therapy may also be used to relieve pain or blockage by shrinking the tumour during palliative care.

Suitable immunotherapies will be known to persons skilled in the art. Illustrative examples of suitable immunotherapies include immune checkpoint inhibitors (e.g., PD-1 inhibitors such as pembrolizumab and nivolumab), CTLA-4 inhibitors (e.g., ipilimumab), cytokines (e.g., interferon- and interleukin-2), oncolytic virus therapy (e.g., talimogene laherparepvec or "T-VEC"), Bacille Calmette-Guerin (BCG) vaccine, imiquimod cream, monoclonal antibodies (e.g., alemtuzumab and trastuzumab) conjugated monoclonal antibodies (e.g., ibritumomab tiuxetan, brentuximab vedotin and ado-trastuzumab emtansine), bispecific monoclonal antibodies (e.g., blinatumomab), denileukin diftitox and tumour-infiltrating lymphocytes (TILs).

Suitable targeted molecular therapies will be known to persons skilled in the art. Illustrative examples of suitable targeted molecular therapies include BRAF inhibitors (e.g., vemurafenib and dabrafenib), MEK inhibitors (e.g., trametinib and cobimetinib), c-KIT inhibitors (e.g., imatinib and nilotinib), tyrosine kinase inhibitors (e.g., pazopanib and axitinib) and mTOR inhibitors (e.g., everolimus).

A determinative factor for selecting a suitable therapeutic regimen for the treatment of melanoma is the stage of progression. For example, for a subject identified as having a more advanced stage of melanoma (as determined, e.g., by Stage assessment), a more aggressive therapeutic regimen may be prescribed as compared, for example, for a subject who has a less advanced melanoma (i.e., Stage 0, I or II), as determined, for example, by the methods disclosed herein.

As described elsewhere herein, therapeutic regimens will typically be designed by a medical practitioner or a team of medical practitioners, having regard, for example, to the age, weight, body mass index and general health of the subject, as noted elsewhere herein.

In some embodiments, the therapeutic regimen comprises a combination of two or more treatment modalities (e.g., 2, 3 or more, 4 or more, 5 or more, 6 or more). Treatment modalities will typically be selected with a view to treating and/or preventing melanoma and/or melanoma recurrence.

As used herein the terms "treat", "treatment", "treating", "prevent", "preventing" and "prevention" refer to any and all uses which remedy a condition or symptom, prevent the establishment of a condition or disease, or otherwise prevent, hinder, retard, abrogate or reverse the onset or progression of a condition or disease or other undesirable symptoms in any way whatsoever. Thus, the terms "treating" and "preventing" and the like are to be considered in their broadest context. For example, treatment does not necessarily imply that a patient is treated until total recovery or cure. In conditions which display or a characterized by multiple symptoms, the treatment or prevention need not necessarily remedy, prevent, hinder, retard, or reverse all of said symptoms, but may prevent, hinder, retard, or reverse one or more of said symptoms. In the context of melanoma, the agents, uses, methods and protocols of the present disclosure that involve treatment or prevention may prevent, reduce, ameliorate or otherwise delay melanoma progression, or of a highly undesirable event associated with melanoma progression or an irreversible outcome of melanoma progression, but may not of itself prevent progression of the melanoma or an outcome associated therewith (e.g., a symptom associated with melanoma). Accordingly, treatment and/or prevention include amelioration of the symptoms of melanoma progression or preventing or otherwise reducing the risk of melanoma progression.

The term "inhibiting" and variations thereof, such as "inhibition" and "inhibits", as used herein, do not necessarily imply the complete inhibition of the specified event, activity or function. Rather, the inhibition may be to an extent, and/or for a time, sufficient to produce the desired effect. Inhibition may be prevention, retardation, reduction, abrogation or otherwise hindrance of an event, activity or function. Such inhibition may be in magnitude and/or be temporal in nature. In particular contexts, the terms "inhibit" and "prevent", and variations thereof may be used interchangeably.

Kits

In another aspect of the present disclosure there is provided a kit comprising one or more reagents and/or devices for use in performing the methods disclosed herein. The kits may contain reagents for analysing the expression of the one or more autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample in accordance with the methods disclosed herein.

Kits for carrying out the methods of the present invention may also include, in suitable container means, (i) one or more reagents for detecting the one or more autoantibodies, (ii) one or more nucleic acid probes that specifically bind to the nucleic acid molecule(s) encoding each of the one or more autoantibodies, (iii) one or more probes that are capable of detecting and/or measuring the expression of the one or more autoantibodies, (iv) one or more labels for detecting the presence of the probes and/or (iv) instructions for how to measure the level of expression of the one or more autoantibodies. The container means of the kits will generally include at least one vial, test tube, flask, bottle, syringe and/or other container into which one or more reagents will be placed or suitably aliquoted. Where a second and/or third and/or additional component is provided, the kit will also generally contain a second, third and/or other additional container into which this component may be placed. Alternatively, a container may contain a mixture of more than one reagent, as required. The kits may also include means for containing the one or more reagents (e.g., nucleic acids) in close confinement for commercial sale. Such containers may include injection and/or blow-moulded plastic containers into which the desired vials are retained.

The kits may further comprise positive and negative controls, including a reference sample, as well as instructions for the use of kit components contained therein, in accordance with the methods disclosed herein.

All essential materials and reagents required for detecting and quantifying the one or more autoantibodies may be assembled together in a kit. The kits may also optionally include appropriate reagents for detection of labels, positive and negative controls, washing solutions, blotting membranes, microtiter plates, dilution buffers and the like. For example, a protein-based detection kit may include (i) one or more of the autoantibodies in the panel of autoantibodies selected from the group consisting of anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 (which may be used as a positive control), (ii) one or more antigens that are specific for the one or more autoantibodies or probes that specifically hybridize to one or more of the autoantibodies. Also included may be fluorescently conjugated monoclonal or polyclonal antibodies for the detection of bound autoantibodies. Such kits may also comprise, in suitable means, distinct containers for each individual reagent and enzyme as well as for each antibody or antigen. The kit may also feature various devices (e.g., one or more) and reagents (e.g., one or more) for performing any one of the assays described herein; and/or printed instructions for using the kit to quantify the expression of the one or more autoantibodies.

It will be appreciated that the above described terms and associated definitions are used for the purpose of explanation only and are not intended to be limiting.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All publications mentioned in this specification are herein incorporated by reference in their entirety.

The present disclosure is further described by reference to the following non-limiting examples.

Examples

Materials and Methods
Study Participants

A total of 245 study participants were recruited by collaborating clinicians and the principal researchers. All participants provided informed consent to participate in this study, previously approved by the Edith Cowan University Ethics Committee (numbers 11543 and 12066). Patients were diagnosed by routine pathological examination of their excised primary tumour and staged according to the TNM staging system for melanoma according to the American Joint Committee on Cancer (AJCC) guidelines (Balch et al., 2009, *Journal of Clinical Oncology*, 27(36): 6199-6206). Healthy volunteers were defined as never having been diagnosed with cancer, melanoma or any autoimmune disease. The study cohort 1 included 104 early-stage melanoma patients (classified as TNM stages in situ, I and II) and 105 healthy volunteers. A smaller cohort consisting of 20 early stage melanoma patients (classified as TNM stages in situ and I only) and 16 healthy volunteers (cohort 2) was used for validation purposes.

The participant characteristics are summarised below in Table 1. The number of males was higher than the number of females in both cohorts and in cohort 1, patients were significantly older than healthy volunteers (mean and standard deviation of 62.5±16.3 versus 56.5±12.9 years, p=0.003), however this was largely due to the difference between the male patients and healthy volunteers (63.7 versus 56.8 years, p=0.004). There was no significant difference in the mean age of female patients relative to controls in cohort 1 (59.8 versus 55.7 years, p=0.309).

TABLE 1

| Group | Cohort 1 | | Cohort 2 | |
|---|---|---|---|---|
| | Early-stage CM patients | Healthy volunteers | Early-stage CM patients | Healthy volunteers |
| total cohort number | 209 | | 36 | |
| sample number | 104 | 105 | 20 | 16 |
| Female, n (%) | 32 (30.8) | 35 (33.3) | 5 (25) | 3 (18.8) |
| Male, n (%) | 72 (69.2) | 70 (66.7) | 15 (75) | 13 (81.2) |
| Mean age ± SD (years) | 62.5 ± 16.3 | 56.5 ± 12.9 | 57.2 ± 13.5 | 55.8 ± 13.4 |
| Age range (years) | 20-96 | 20-83 | 26-76 | 25-80 |
| TNM stage, n (%) | | | | |
| 0 (insitu) | 45 (43.3) | | 15 (75) | |
| I | 38 (36.5) | | 5 (25) | |
| II | 21 (20.2) | | 0 (0) | |
| Primary tumour site, n (%) | | | | |
| Head and Neck | 15 (14.4) | | 4 (20) | |
| Trunk | 43 (41.3) | | 9 (45) | |
| Extremities | 40 (38.5) | | 7 (35) | |
| Multiple primary melanoma with multiple tumour sites | 5 (4.8) | | 0 (0) | |
| not reported | 1 (1.0) | | 0 (0) | |
| Melanoma subtype, n (%) | | | | |
| SSM | 13 (12.5) | | 3 (15) | |
| NM | 5 (4.8) | | 0 (0) | |
| LMM | 8 (7.7) | | 0 (0) | |
| ALM | 0 (0) | | 0 (0) | |
| multiple CM subtypes | 3 (2.9) | | 0 (0) | |
| unclassified | 2 (24) | | 9 (45) | |
| not reported | 50 (48.1) | | 8 (40) | |
| Ulceration, n (%) | | | | |
| present | 20 (19.2) | | 4 (20) | |
| absent | 57 (54.8) | | 14 (70) | |
| not reported | 27 (26) | | 2 (10) | |
| Regression, n (%) | | | | |
| present | 36 (34.6) | | 7 (35) | |
| absent | 22 (21.2) | | 3 (15) | |
| not reported | 46 (44.2) | | 10 (50) | | numbers are rounded to 1 decimal;
SD, standard deviation;
CM, cutaneous melanoma;
SSM, superficial spreading melanoma;
NM, nodular melanoma;
LMM, lentigo maligna melanoma;
ALM, acral lentiginous melanoma Sample Collection A once-off blood sample was obtained from all study participants. For melanoma patients, the sample was obtained at the time, or within 3 months, of patient primary tumour diagnosis and excision. Venous blood from all study participants was collected into one 8.5 ml serum separator tube (SST) (BD, New Jersey, United States). The blood was allowed to clot at room temperature for a minimum of 30 mins and was centrifuged at 1600 g for 10 mins. A small number of healthy volunteer samples (n=8) which had been collected into EDTA tubes were analysed from plasma.

These samples were included in this study as serum and plasma samples have previously been found to yield comparable results in functional protein microarray studies (Gnjantic et al., supra). Samples were processed within 24 hours. Following centrifugation, serum was aliquoted and stored at −80° C. until further use or until it was shipped to Sengenics, University of Malaysia, Kuala Lumpur, Malaysia, for the microarray screening of cohort 1 or to Oxford Gene Technology (OGT), Oxfordshire, United Kingdom, for the microarray screening of cohort 2. Both locations utilised the same microarray platform (OGT, UK) and Sengenics staff received training as well as ongoing advice from OGT directly. OGT and Sengenics staff were blinded to the fact that, for the purpose of cross-validation between the two screening sites, identical aliquots from 16 randomly selected patients and 11 healthy control samples were screened at both sites, and showed comparable results (rho >0.5, Table 2) enabling the use of cohort 2 as an independent validation cohort.

tion. All arrays were scanned at 10 μm resolution using a microarray scanner (Axon 4200AL with GenePix Pro Software, Molecular Devices, Sunnyvale, Calif., USA) and fluorescence of labelled IgG was detected according to the manufacturer's instructions. Images were saved as 16-bit tiff files and analysis was performed using GenePix software. Interaction between microarray antigens and serum autoantibodies was detected as fluorescence of the bound fluorescently-labelled IgG at the protein specific position on the microarray. The intensity of fluorescence is proportional to the amount of autoantibody present in the serum. Local background obtained from control spots on the array was subtracted automatically and relative fluorescence units (rfu) for each microarray spot were recorded. Each antigen was immobilised in quadruplicate on the array. The median rfu for the four readings of each antigen was utilised for further analysis. A reference serum was included in each microarray experiment run. Arrays that did not pass quality control tests were repeated or the spots were realigned in the software or excluded. Thereafter, arrays were excluded from the analysis if they did not pass quality control.

TABLE 2

| Sample ID | Correlation coefficient (rho) of twice (intra- and inter-array) normalised data | p-value | Correlation coefficient (rho) of once (intra-array) normalised data | p-value | Correlation coefficient (rho) of raw data | p-value |
| --- | --- | --- | --- | --- | --- | --- |
| CM17 | 0.769 | <0.001 | | | | |
| CM1 | 0.545 | <0.001 | | | | |
| CM10 | 0.849 | <0.001 | | | | |
| CM12 | 0.076 | 0.372 | | | | |
| CM13 | 0.847 | <0.001 | | | | |
| CM14 | 0.605 | <0.001 | | | | |
| CM15 | 0.803 | <0.001 | | | | |
| CM19 | 0.750 | <0.001 | | | | |
| CM22 | 0.711 | <0.001 | | | | |
| CM24 | 0.851 | <0.001 | | | | |
| CM25 | 0.605 | <0.001 | | | | |
| CM3 | 0.586 | <0.001 | | | | |
| CM5 | 0.921 | <0.001 | | | | |
| CM6 | 0.808 | <0.001 | | | | |
| CM7 | 0.892 | <0.001 | | | | |
| CM8 | 0.712 | <0.001 | | | | |
| HC14 | 0.583 | <0.001 | | | | |
| HC17 | 0.579 | <0.001 | | | | |
| HC20 | 0.687 | <0.001 | | | | |
| HC22 | 0.699 | <0.001 | | | | |
| HC23 | 0.374 | <0.001 | | | | |
| HC25 | 0.628 | <0.001 | | | | |
| HC27 | 0.799 | <0.001 | | | | |
| HC28 | 0.678 | <0.001 | | | | |
| HC29 | 0.771 | <0.001 | | | | |
| HC30 | 0.220 | 0.009 | | | | |
| HC32 | 0.487 | <0.001 | | | | |

A total of 16 patient (CM) and 11 healthy control (HC) samples were run in both study cohorts, rho and p-values obtained through Spearman's Rho correlation, p < 0.05 was considered significant (bold)

Protein Microarray Profiling

The functional protein microarray was developed and constructed by Oxford Gene Technology (OGT), Oxfordshire, United Kingdom. Patient or control serum samples were diluted 1:200 in 2 ml buffer (0.1% Triton X100 (v/v), 0.1% BSA (w/v) in PBS) and applied to the array (one array per sample). The arrays were incubated in Quadriperm dishes (Greiner BioOne, Stonehouse, UK) and placed on a horizontal shaker at 50 rpm for a period of 2 hours at room temperature. After several washes, anti-human IgG was diluted 1:1000 in assay buffer and Cy3-rabbit anti-human IgG (Dako Cytomation) by incubation for 2 hours at room temperature according to the manufacturer's recommendations. The plate was washed again and dried by centrifuga- Statistical Analysis
Data Normalisation Intra- and inter-array data normalisation was performed to ensure data comparability between samples. First, the overall median value of all median rfu values of the 1627 printed proteins (excluding data from controls spots) was calculated and intra-array normalisation was achieved by dividing the median of the quadruplicate spots of each protein on the array, by the overall median value of all the proteins on the array in each sample. Inter-array normalisation was achieved by utilisation of the normalize.quantiles package in R (Bolstad et al., supra).

Selection of Melanoma Associated Autoantibodies

Once normalised, a data analysis approach, as performed by Gnjatic et al. (supra) was utilised to determine the proteins with the highest and most frequent seroreactivity in patient samples relative to healthy volunteer sera. This was achieved by calculating the interquartile range (IQR) for each protein to establish a cutoff. This cutoff (2.5×IQR above the 75$^{th}$ percentile) was used to dichotomise the data, whereby a value was defined as positive (for seroreactivity) if it was above the cut-off; otherwise it was defined as negative. This criterion was used to ensure false positive data was minimised while providing increased specificity and sensitivity. For cases with positive seroreactivity, the ratio between the signal and cutoff (S/C ratio) was calculated. Thereafter, the average S/C ratio was calculated per biomarker for each cohort, i.e., melanoma patient or healthy control.

Finally, a "biomarker score" was assigned to each protein by multiplying the number of positive samples by the cubic root of the corresponding S/C ratio average. This score is a reflection of the strength and frequency of the signal in patients relative to healthy subjects. The proteins were then ranked based on the differences in the biomarker scores (patients—healthy controls). A large AAb biomarker score (>5) indicates that most seroreactivity is attributable to the patients. This reduced the number of potential diagnostic melanoma autoantibody biomarkers from 1627 to 139 in cohort 1 (Table 3).

Selection of Biomarker Panel

Combinations of identified biomarkers, rather than individual biomarkers for early melanoma detection, were assessed to achieve greater sensitivity and specificity. The classification tree method was selected for this task and this analysis was performed using data from cohort 1 only as cohort 2 was not sufficiently powered. The number of variables (i.e., 139 antigens) at this stage was still reasonably large relative to the overall sample size. To avoid the possibility of overfitting, a two-stage process was utilised, as follows:

Stage 1 involved the use of random forest regression analysis (Brieman, 2001) for identifying key biomarker proteins and to further reduce the number of biomarkers in contention for the next modelling stage. Stage 2 utilised the classical classification tree approach (Brieman, 1984) to develop a tree model based on the reduced list of biomarkers.

All analyses were implemented with the R software package (Version 3.2.2; R Core Team, 2013). The key R packages used were randomForest (Liaw & Wiener, 2002, R News, 2: 18-22), rpart (Therneau et al., 2015) and caret (Kuhn, 2015).

Additional Statistical Analysis

To test whether the data was approximately normally distributed, a Shapiro-Wilk's test (p>0.05; Shapiro & Wilk, 1965, *Biometrica*, 52(3/4): 591-611), visual inspection of histograms, normal Q-Q plots and box-plots were performed. The majority of the data in this study was not normally distributed. To assess whether AAb serum scores and other continuous measures varied between levels between two independent groups of samples (i.e., patients and healthy controls), a Mann-Whitney U test or the parametric equivalent independent t-test was used. For this analysis, a "serum score" was calculated from the twice normalised data for each sample by determining the sum of all signal intensities above the antigen-associated cut off for each protein of interest (Zayakin et al., supra). For comparison of categorical covariates between groups such as TNM stage, gender, tumour location and others, Chi-square or Fisher's exact tests were utilised. To assess whether various patient demographics or features of their primary tumour were accountable for changes in the patient serum scores of the identified top 139 biomarkers as well as the frequency of positive AAb responses in each patient, Bivariate Spearman's Rho correlation analysis was performed. Sensitivity and specificity of individual and combinations of AAbs were evaluated by ROC. These analyses were performed using Microsoft Excel, SPSS statistical software (version 22.0) and GraphPad Prism (version 5). A p-value of <0.05 was defined as statistically significant.

Finally, to explore the biological relevance of the identified autoantibody biomarkers and their interactions, we submitted the top 139 antigen names to STRING the online functional protein association network in order to explore the main shared antigen pathways at medium protein interaction confidence of 0.400. The submitted protein names are identical to Table 3 while protein PCTK1 and SDCCAD10 were searched by their alternative names CDK16 and CWC27, respectively.

Results (A) the Expression of One or More Autoantibodies Correlates with Early Stage Melanoma In cohort 1, a total of 748 antigens reacted preferentially with the patient sera as indicated by their positive biomarker scores. Of those, 139 resulted in scores of 5 or greater and were therefore considered to have a potential diagnostic value (Table 3). The majority of the identified 139 antigens displayed very high specificity ranging from 86.7%-100% (mean of 97%), while their sensitivity as single biomarker ranged from 2.9% to 18.3% (mean of 9.9%). Notably, 20/139 (14.4%) antigens did not react with any of the healthy control samples. Most of the identified markers are novel and are not known for their association with melanoma. It is, however, important to note that many were reactive against, transcription factors that may influence an array of cancer-related pathways, tumour suppressors and promoters, markers of apoptosis, and regulators of pigmentation and T-cell differentiation. Some of the top 139 seroreactive antigens such as VEGFb, p53, KIT and MLANA have previously been associated with melanoma or cancer in general, thus supporting that the detected autoantibody response is derived from an anti-tumour response.

TABLE 3

| Protein | Sensitivity (%) | Specificity (%) | cutoff | average signal to cutoff ratio for patients | average signal to cutoff ratio for healthy volunteers | overall score patients | overall score healthy volunteers | difference in cohort scores (patients – healthy volunteers) |
|---|---|---|---|---|---|---|---|---|
| PRKCH | 18.3 | 95.2 | 1.21 | 3.73 | 1.44 | 29.47 | 5.65 | 23.82 |
| PCTK3 | 16.3 | 96.2 | 1.25 | 7.42 | 20.62 | 33.16 | 10.97 | 22.19 |
| DPF2 | 15.4 | 96.2 | 1.47 | 5.59 | 4.75 | 28.40 | 6.72 | 21.68 |

TABLE 3-continued

| Protein | Sensitivity (%) | Specificity (%) | cutoff | average signal to cutoff ratio for patients | average signal to cutoff ratio for healthy volunteers | overall score patients | overall score healthy volunteers | difference in cohort scores (patients − healthy volunteers) |
|---|---|---|---|---|---|---|---|---|
| KIT | 17.3 | 95.2 | 1.06 | 2.50 | 2.36 | 24.42 | 6.65 | 17.77 |
| KLK3 | 16.3 | 95.2 | 1.25 | 2.53 | 2.24 | 23.16 | 6.54 | 16.62 |
| STK38L | 15.4 | 95.2 | 1.60 | 3.21 | 2.85 | 23.60 | 7.09 | 16.50 |
| STMN1 | 16.3 | 92.4 | 2.65 | 3.38 | 1.47 | 25.51 | 9.11 | 16.41 |
| DLX3 | 16.3 | 98.1 | 0.96 | 1.11 | 1.14 | 17.60 | 2.09 | 15.51 |
| ZBTB7B | 16.3 | 98.1 | 0.92 | 1.13 | 1.49 | 17.71 | 2.29 | 15.43 |
| ASB1 | 16.3 | 95.2 | 1.17 | 2.00 | 1.76 | 21.43 | 6.04 | 15.40 |
| CASP7 | 14.4 | 95.2 | 1.64 | 4.27 | 6.22 | 24.33 | 9.19 | 15.14 |
| RAC2 | 16.3 | 96.2 | 1.10 | 1.56 | 1.78 | 19.70 | 4.85 | 14.85 |
| HBG1 | 13.5 | 98.1 | 1.14 | 1.73 | 1.16 | 16.81 | 2.10 | 14.71 |
| NFE2L2 | 15.4 | 98.1 | 1.14 | 1.11 | 1.09 | 16.56 | 2.06 | 14.50 |
| ELK1 | 12.5 | 97.1 | 3.52 | 2.64 | 1.65 | 17.97 | 3.54 | 14.43 |
| EZH2 | 15.4 | 98.1 | 1.03 | 1.09 | 1.33 | 16.47 | 2.20 | 14.27 |
| PDGFRL | 18.3 | 93.3 | 1.07 | 1.64 | 1.58 | 22.42 | 8.15 | 14.27 |
| HRH2 | 16.3 | 93.3 | 1.20 | 2.54 | 2.14 | 23.19 | 9.02 | 14.17 |
| TP53 | 10.6 | 98.1 | 5.79 | 3.15 | 1.19 | 16.12 | 2.12 | 14.01 |
| EXT2 | 17.3 | 95.2 | 1.09 | 1.20 | 1.16 | 19.12 | 5.25 | 13.87 |
| PYGO2 | 13.5 | 94.3 | 1.90 | 3.29 | 1.83 | 20.83 | 7.34 | 13.48 |
| SERPINB5 | 14.4 | 98.1 | 1.02 | 1.14 | 1.32 | 15.68 | 2.20 | 13.48 |
| NR1I2 | 13.5 | 99 | 0.99 | 1.11 | 1.11 | 14.49 | 1.04 | 13.46 |
| XYLB | 16.3 | 95.2 | 1.48 | 1.32 | 1.24 | 18.67 | 5.37 | 13.31 |
| PHIP | 16.3 | 95.2 | 1.22 | 1.31 | 1.30 | 18.59 | 5.46 | 13.13 |
| CCNB1 | 10.6 | 96.2 | 3.10 | 4.43 | 2.17 | 18.07 | 5.18 | 12.89 |
| STAT5A | 13.5 | 97.1 | 1.05 | 1.44 | 1.09 | 15.81 | 3.09 | 12.72 |
| RAD23B | 15.4 | 94.3 | 3.16 | 1.92 | 1.82 | 19.88 | 7.33 | 12.55 |
| IFI16 | 13.5 | 98.1 | 1.03 | 1.14 | 1.27 | 14.62 | 2.16 | 12.45 |
| TUBB | 10.6 | 97.1 | 1.18 | 3.40 | 2.78 | 16.54 | 4.22 | 12.33 |
| SMARCE1 | 16.3 | 94.3 | 0.80 | 1.34 | 1.28 | 18.73 | 6.52 | 12.21 |
| MSN | 9.6 | 98.1 | 2.42 | 2.92 | 1.90 | 14.29 | 2.48 | 11.81 |
| ZNF169 | 10.6 | 98.1 | 1.31 | 2.34 | 2.77 | 14.60 | 2.81 | 11.79 |
| HSPA1A | 10.6 | 97.1 | 1.48 | 2.55 | 1.28 | 15.04 | 3.26 | 11.78 |
| DR1 | 14.4 | 91.4 | 1.71 | 3.07 | 1.40 | 21.80 | 10.07 | 11.73 |
| SLC25A6 | 14.4 | 95.2 | 1.09 | 1.42 | 1.48 | 16.86 | 5.69 | 11.17 |
| TRAF2 | 9.6 | 98.1 | 4.39 | 2.13 | 1.18 | 12.87 | 2.11 | 10.76 |
| BAD | 16.3 | 94.3 | 1.45 | 2.82 | 11.15 | 24.03 | 13.41 | 10.62 |
| PKNOX1 | 9.6 | 98.1 | 6.32 | 2.15 | 2.00 | 12.91 | 2.52 | 10.39 |
| PCTK1 | 11.5 | 97.1 | 6.05 | 1.65 | 2.35 | 14.19 | 3.99 | 10.20 |
| FOXR2 | 17.3 | 91.4 | 5.94 | 1.98 | 2.70 | 22.60 | 12.53 | 10.06 |
| EZR | 7.7 | 98.1 | 2.09 | 3.39 | 1.22 | 12.02 | 2.14 | 9.88 |
| PPP2CB | 12.5 | 96.2 | 1.45 | 1.33 | 1.41 | 14.31 | 4.49 | 9.82 |
| UBE2V1 | 4.8 | 99 | 1.70 | 9.97 | 1.27 | 10.76 | 1.08 | 9.68 |
| JUNB | 10.6 | 98.1 | 1.18 | 1.20 | 1.16 | 11.69 | 2.10 | 9.60 |
| BIRC7 | 12.5 | 95.2 | 3.46 | 1.63 | 1.59 | 15.31 | 5.83 | 9.48 |
| STK10 | 9.6 | 98.1 | 1.81 | 1.53 | 1.31 | 11.53 | 2.19 | 9.35 |
| DSTYK | 13.5 | 95.2 | 1.18 | 1.10 | 1.12 | 14.45 | 5.19 | 9.26 |
| MTERF | 10.6 | 98.1 | 0.99 | 1.13 | 1.86 | 11.46 | 2.46 | 9.00 |
| FEN1 | 8.7 | 92.4 | 4.47 | 8.88 | 1.86 | 18.64 | 9.85 | 8.79 |
| KLF12 | 7.7 | 100 | 1.24 | 1.28 | 0.00 | 8.68 | 0.00 | 8.68 |
| MEF2A | 9.6 | 96.2 | 2.23 | 2.97 | 3.01 | 14.37 | 5.77 | 8.60 |
| SCFD1 | 8.7 | 97.1 | 1.49 | 2.37 | 1.46 | 12.00 | 3.40 | 8.60 |
| ZNF444 | 8.7 | 99 | 1.08 | 1.21 | 1.06 | 9.60 | 1.02 | 8.58 |
| STAP1 | 13.5 | 92.4 | 3.61 | 2.29 | 1.93 | 18.45 | 9.96 | 8.49 |
| CDK2 | 9.6 | 96.2 | 3.94 | 2.41 | 1.86 | 13.41 | 4.92 | 8.49 |
| NFYA | 8.7 | 98.1 | 1.30 | 1.62 | 1.15 | 10.56 | 2.10 | 8.47 |
| TGIF1 | 8.7 | 99 | 1.26 | 1.12 | 1.09 | 9.36 | 1.03 | 8.33 |
| RPL32 | 10.6 | 97.1 | 1.28 | 1.11 | 1.10 | 11.38 | 3.10 | 8.29 |
| DLX1 | 7.7 | 100 | 1.09 | 1.10 | 0.00 | 8.26 | 0.00 | 8.26 |
| XBP1 | 9.6 | 98.1 | 1.07 | 1.17 | 1.57 | 10.54 | 2.32 | 8.22 |
| IMPA1 | 8.7 | 99 | 1.51 | 1.08 | 1.08 | 9.22 | 1.03 | 8.20 |
| PLD2 | 9.6 | 98.1 | 1.06 | 1.07 | 1.17 | 10.23 | 2.11 | 8.12 |
| ACVR2A | 15.4 | 90.5 | 2.23 | 2.18 | 2.03 | 20.75 | 12.66 | 8.09 |
| PQBP1 | 9.6 | 97.1 | 2.99 | 1.40 | 1.42 | 11.18 | 3.37 | 7.81 |
| TTF2 | 5.8 | 100 | 1.27 | 2.16 | 0.00 | 7.76 | 0.00 | 7.76 |
| USH1C | 7.7 | 98.1 | 4.74 | 1.90 | 1.42 | 9.91 | 2.25 | 7.67 |
| HEXIM1 | 7.7 | 97.1 | 1.82 | 2.43 | 1.11 | 10.76 | 3.10 | 7.66 |
| LRRFIP2 | 10.6 | 95.2 | 4.45 | 2.15 | 2.32 | 14.19 | 6.62 | 7.58 |
| CEP55 | 7.7 | 99 | 2.29 | 1.21 | 1.01 | 8.52 | 1.00 | 7.52 |
| SCAND1 | 5.8 | 97.1 | 1.42 | 5.65 | 1.21 | 10.69 | 3.20 | 7.49 |
| VEGFB | 7.7 | 97.1 | 3.24 | 2.75 | 2.03 | 11.21 | 3.80 | 7.41 |
| HEYL | 6.7 | 100 | 1.20 | 1.18 | 0.00 | 7.41 | 0.00 | 7.41 |
| RQCD1 | 6.7 | 99 | 2.71 | 1.81 | 1.53 | 8.53 | 1.15 | 7.38 |
| SDCCAG10 | 11.5 | 93.3 | 3.08 | 2.16 | 1.56 | 15.50 | 8.12 | 7.38 |
| MLANA | 5.8 | 98.1 | 2.59 | 4.27 | 1.77 | 9.73 | 2.42 | 7.32 |

TABLE 3-continued

| Protein | Sensitivity (%) | Specificity (%) | cutoff | average signal to cutoff ratio for patients | average signal to cutoff ratio for healthy volunteers | overall score patients | overall score healthy volunteers | difference in cohort scores (patients − healthy volunteers) |
|---|---|---|---|---|---|---|---|---|
| HNF1B | 6.7 | 100 | 1.16 | 1.14 | 0.00 | 7.31 | 0.00 | 7.31 |
| MAPK8_tv2 | 5.8 | 99 | 2.60 | 2.72 | 1.26 | 8.37 | 1.08 | 7.30 |
| PSME2 | 6.7 | 98.1 | 2.01 | 2.42 | 1.21 | 9.40 | 2.13 | 7.27 |
| NDRG2 | 7.7 | 98.1 | 2.12 | 1.63 | 1.24 | 9.41 | 2.15 | 7.26 |
| FOXA3 | 6.7 | 100 | 1.31 | 1.11 | 0.00 | 7.26 | 0.00 | 7.26 |
| CKB | 3.8 | 100 | 3.68 | 5.94 | 0.00 | 7.24 | 0.00 | 7.25 |
| ZNF449 | 7.7 | 99 | 1.17 | 1.07 | 1.02 | 8.19 | 1.01 | 7.18 |
| PBX1 | 8.7 | 98.1 | 1.06 | 1.07 | 1.05 | 9.21 | 2.03 | 7.18 |
| TPM1 | 8.7 | 97.1 | 9.02 | 1.86 | 2.19 | 11.06 | 3.90 | 7.17 |
| NME5 | 8.7 | 97.1 | 1.63 | 2.17 | 3.87 | 11.65 | 4.71 | 6.94 |
| GTF2A2 | 8.7 | 98.1 | 1.08 | 1.05 | 1.45 | 9.16 | 2.26 | 6.90 |
| CCND1 | 4.8 | 100 | 1.66 | 2.53 | 0.00 | 6.81 | 0.00 | 6.81 |
| PAPSS2 | 7.7 | 98.1 | 5.97 | 1.67 | 2.59 | 9.49 | 2.75 | 6.75 |
| STAT4 | 7.7 | 98.1 | 2.59 | 1.57 | 2.25 | 9.31 | 2.62 | 6.68 |
| CBFA2T3 | 15.4 | 89.5 | 4.14 | 2.80 | 3.01 | 22.54 | 15.89 | 6.66 |
| HMGB2 | 8.7 | 94.3 | 1.89 | 2.93 | 1.19 | 12.88 | 6.35 | 6.53 |
| CCDC33 | 8.7 | 97.1 | 2.57 | 1.85 | 3.46 | 11.04 | 4.54 | 6.51 |
| AK2 | 6.7 | 98.1 | 2.29 | 2.16 | 2.25 | 9.04 | 2.62 | 6.42 |
| SMAD2 | 7.7 | 98.1 | 3.61 | 1.44 | 2.23 | 9.03 | 2.61 | 6.42 |
| FMR1NB | 6.7 | 99 | 1.53 | 1.13 | 1.04 | 7.30 | 1.01 | 6.29 |
| FAF1 | 9.6 | 95.2 | 2.89 | 2.30 | 2.68 | 13.21 | 6.95 | 6.26 |
| CREB5 | 6.7 | 99 | 1.29 | 1.11 | 1.03 | 7.24 | 1.01 | 6.23 |
| ZFP36L1 | 6.7 | 99 | 1.20 | 1.11 | 1.05 | 7.24 | 1.01 | 6.22 |
| IRF4 | 5.8 | 100 | 2.59 | 1.11 | 0.00 | 6.22 | 0.00 | 6.22 |
| PTPN20A | 14.4 | 89.5 | 3.87 | 2.46 | 2.08 | 20.26 | 14.04 | 6.21 |
| C1orf216 | 5.8 | 98.1 | 2.58 | 2.57 | 1.02 | 8.22 | 2.01 | 6.21 |
| HSFY1 | 5.8 | 100 | 1.07 | 1.09 | 0.00 | 6.17 | 0.00 | 6.17 |
| KIF9 | 4.8 | 98.1 | 1.13 | 4.89 | 1.57 | 8.49 | 2.32 | 6.17 |
| RING1 | 5.8 | 99 | 1.32 | 1.70 | 1.03 | 7.17 | 1.01 | 6.15 |
| PRDM4 | 6.7 | 99 | 1.13 | 1.22 | 2.31 | 7.48 | 1.32 | 6.15 |
| MAFG | 7.7 | 98.1 | 1.16 | 1.14 | 1.35 | 8.36 | 2.21 | 6.15 |
| MECP2 | 7.7 | 98.1 | 1.09 | 1.11 | 1.24 | 8.29 | 2.15 | 6.14 |
| HOXB6 | 7.7 | 98.1 | 1.09 | 1.14 | 1.41 | 8.36 | 2.24 | 6.11 |
| MUTYH | 6.7 | 99 | 1.09 | 1.08 | 1.59 | 7.17 | 1.17 | 6.01 |
| CDC25A | 4.8 | 100 | 1.72 | 1.64 | 0.00 | 5.90 | 0.00 | 5.90 |
| CDKN2C | 5.8 | 99 | 1.88 | 1.53 | 1.23 | 6.92 | 1.07 | 5.85 |
| SUPT4H1 | 2.9 | 100 | 1.83 | 6.94 | 0.00 | 5.72 | 0.00 | 5.72 |
| CHEK2 | 5.8 | 99 | 1.71 | 1.49 | 1.87 | 6.85 | 1.23 | 5.62 |
| BIRC5 | 5.8 | 99 | 2.18 | 1.35 | 1.30 | 6.64 | 1.09 | 5.55 |
| INPP1 | 6.7 | 98.1 | 1.53 | 2.92 | 11.15 | 10.01 | 4.47 | 5.54 |
| TXN2 | 12.5 | 91.4 | 3.37 | 2.16 | 1.97 | 16.81 | 11.28 | 5.53 |
| CBLC | 4.8 | 99 | 3.14 | 2.51 | 2.04 | 6.79 | 1.27 | 5.52 |
| ANXA11 | 8.7 | 94.3 | 1.76 | 2.58 | 1.51 | 12.35 | 6.89 | 5.46 |
| MAX | 8.7 | 93.3 | 2.59 | 3.71 | 1.78 | 13.94 | 8.48 | 5.46 |
| SLCO6A1 | 7.7 | 97.1 | 1.59 | 1.29 | 1.38 | 8.71 | 3.34 | 5.37 |
| EEF1D | 6.7 | 98.1 | 4.94 | 1.23 | 1.23 | 7.49 | 2.14 | 5.35 |
| TLX2 | 4.8 | 100 | 1.16 | 1.20 | 0.00 | 5.31 | 0.00 | 5.31 |
| HORMAD1 | 4.8 | 100 | 1.28 | 1.19 | 0.00 | 5.30 | 0.00 | 5.30 |
| CTNNA2 | 7.7 | 94.3 | 2.50 | 3.55 | 1.54 | 12.20 | 6.92 | 5.28 |
| GTF2H1 | 7.7 | 97.1 | 0.97 | 1.26 | 1.41 | 8.65 | 3.37 | 5.28 |
| HCFC2 | 9.6 | 95.2 | 1.05 | 1.11 | 1.08 | 10.36 | 5.12 | 5.24 |
| TBX6 | 4.8 | 100 | 1.09 | 1.13 | 0.00 | 5.21 | 0.00 | 5.21 |
| PATZ1 | 5.8 | 99 | 1.08 | 1.09 | 1.02 | 6.18 | 1.01 | 5.17 |
| BTG3 | 4.8 | 100 | 1.01 | 1.10 | 0.00 | 5.17 | 0.00 | 5.17 |
| PDPK1 | 14.4 | 86.7 | 3.29 | 4.43 | 2.69 | 24.63 | 19.47 | 5.16 |
| WAS | 4.8 | 100 | 1.38 | 1.09 | 0.00 | 5.14 | 0.00 | 5.14 |
| TBK1 | 4.8 | 100 | 1.30 | 1.08 | 0.00 | 5.13 | 0.00 | 5.13 |
| TBX5 | 4.8 | 100 | 1.03 | 1.08 | 0.00 | 5.12 | 0.00 | 5.12 |
| NLK | 12.5 | 92.4 | 2.36 | 1.42 | 1.67 | 14.61 | 9.50 | 5.11 |
| MEOX2 | 4.8 | 100 | 1.16 | 1.06 | 0.00 | 5.10 | 0.00 | 5.10 |
| STUB1 | 8.7 | 94.3 | 3.63 | 2.70 | 1.91 | 12.53 | 7.44 | 5.08 |
| BAG3 | 6.7 | 98.1 | 7.03 | 1.26 | 1.97 | 7.56 | 2.51 | 5.05 |
| GMEB1 | 10.6 | 92.4 | 1.66 | 2.71 | 2.14 | 15.34 | 10.31 | 5.03 |

Figure 2:
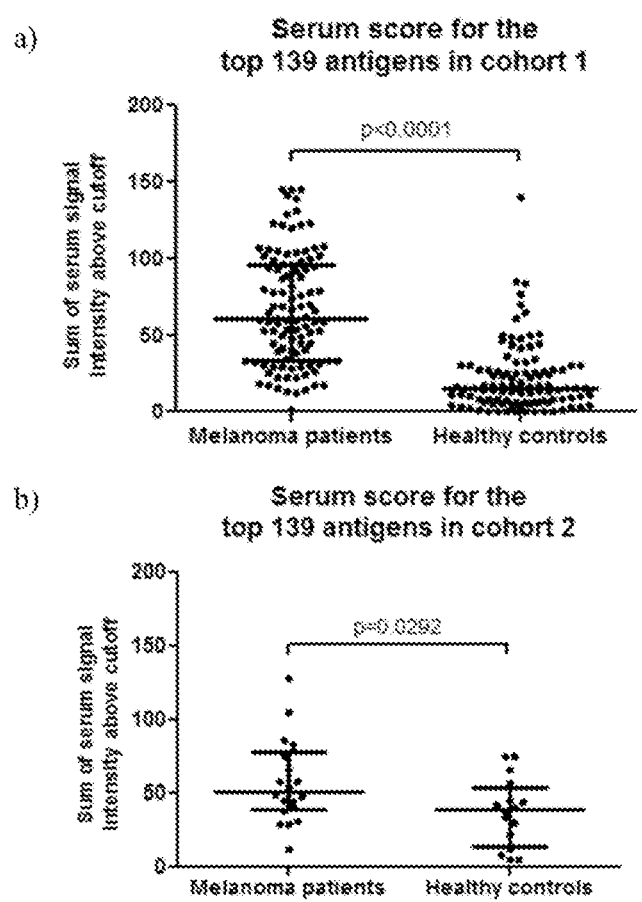
FIG. 2 is a graphical representation of serum scores (y-axis) in melanoma patients and healthy controls (x-axis) for the top 139 individual melanoma-associated biomarkers in (A) cohort 1 and (B) cohort 2. Horizontal lines represent the median and interquartile range (IQR) of all serum scores with dots representing individual samples. Statistical significance was determined by Mann-Whitney U test.

As mentioned in the materials and methods section, "serum scores" were calculated for each sample using the twice normalised data by calculating the sum of all signal intensities above the antigen-associated cut off for each of the top 139 antigens to compare the overall seroreactivity levels between the patient and control cohort. For melanoma patients, the median serum score was 60.5 (IQR 33.9-95.9) and 15.5 (IQR 6.7-27.7) for healthy controls, a highly statistically significant difference ($p<0.0001$, FIG. 2A).

To evaluate the diagnostic performance of the identified biomarkers in a different cohort of samples, we calculated the serum scores for the top 139 biomarkers using the 36 samples included in cohort 2. Patient serum scores were again significantly higher, with a median of 51.1 (IQR 38.7-77.7) compared to healthy control median serum score of 38.9 (IQR 14.1-53.7, p=0.029, FIG. 2B), supporting the validity of the top 139 biomarkers.

The breadth of AAb responses against the protein microarray of 1627 proteins varied between samples. Positive autoantibody production in a sample was defined as a fluorescence reading above the protein associated cut off. Positive autoantibody production to at least one of the proteins was observed in every study participant sample in cohort 1. Out of the 1627 antigens on the array, patient sera reacted with a median of 46.0 (IQR 36.0-70.0) antigens while healthy control sera reacted with a median of 48.0 (IQR 40.5-57.0) antigens (p=0.857). 100% of patient samples and 92.4% of healthy control samples reacted with at least one of the top 139 antigens. In total, a sum of 1426 positive antibody responses against the top 139 antigens were observed in the 104 patients while only 434 positive antibody responses were observed in the 105 healthy controls. A statistically significant difference was observed between the number of individual patient and healthy control sample AAb responses against the 139 antigens (median of 9.0 (IQR 6.0-22.0) versus 3.0 (IQR 1.0-4.0), respectively, p<0.001). The median number of AAb responses was also significantly different between patient and healthy control samples for the identified AAb biomarker combination of 10 autoantibodies, with patient samples displaying a median of 1.0 (IQR 1.0-1.0, range 0-3.0) when compared the control median of 0 (IQR 0-0, range 0-2.0), p<0.001.

None of the patient characteristics or features of the corresponding primary tumour correlated with the serum score or frequency of positive AAb reactions against the top 139 antigens (Table 5). We observed a strong correlation between the tumour mitotic rate and Breslow thickness (r=0.500, p<0.001) as well as between TNM stage and Breslow thickness (r=0.903, p<0.001). Serum scores and frequency of positive AAb responses also displayed a strong correlation (r=0.776, p<0.001) as expected since the serum score is calculated based on the positive AAb serum reactions. Other weak and moderate correlations were observed, including a moderate correlation between patient age and whether a patient was diagnosed with multiple melanoma throughout their life (r=0.362, p<0.001). Since the risk of further melanoma development increases with age, it is not surprising that these measures correlate. Interestingly, we observed a moderate negative correlation between the presence of multiple melanomas and the presence of tumour regression (r=−0.304, p=0.002).

TABLE 5

| | | | Serum scores (top 139 markers) | age in years | TNM stage | gender | tumour site | presence of ulceration |
|---|---|---|---|---|---|---|---|---|
| Spearman's rho | Serum scores (top 139 markers) | Correlation Coefficient | 1.000 | −.097 | .103 | −.017 | .073 | .011 |
| | | Sig (2-tailed) | — | .327 | .298 | .861 | .459 | .595 |
| | | N | 104 | 104 | 104 | 104 | 104 | 104 |
| | age in years | Correlation Coefficient | −.097 | 1.000 | .262** | .108 | −.113 | −.106 |
| | | Sig (2-tailed) | .327 | — | .007 | .274 | .253 | .285 |
| | | N | 104 | 104 | 104 | 104 | 104 | 104 |
| | TNM stage | Correlation Coefficient | −.097 | 1.000 | .262** | .108 | −.113 | −.106 |
| | | Sig (2-tailed) | .298 | .007 | — | .952 | .476 | .068 |
| | | N | 104 | 104 | 104 | 104 | 104 | 104 |
| | gender | Correlation Coefficient | −.017 | .108 | .006 | 1.000 | −.078 | −.017 |
| | | Sig (2-tailed) | .298 | .007 | — | .952 | .476 | .068 |
| | | N | 104 | 104 | 104 | 104 | 104 | 104 |
| | tumour site | Correlation Coefficient | .073 | −.113 | .071 | −.078 | 1.000 | .041 |
| | | Sig (2-tailed) | .459 | .253 | .476 | .432 | — | .680 |
| | | N | 104 | 104 | 104 | 104 | 104 | 104 |
| | presence of ulceration | Correlation Coefficient | −.011 | −.106 | −.179 | −.017 | .041 | 1.000 |
| | | Sig (2-tailed) | .914 | .285 | .068 | .862 | .680 | — |
| | | N | 104 | 104 | 104 | 104 | 104 | 104 |
| | presence of pregression | Correlation Coefficient | .053 | −.123 | −.066 | −.233* | .095 | .245* |
| | | Sig (2-tailed) | .595 | .213 | .506 | .017 | .340 | .012 |
| | | N | 104 | 104 | 104 | 104 | 104 | 104 |
| | miotic rate | Correlation Coefficient | .100 | .25** | .443** | .067 | −.144 | −.327 |
| | | Sig (2-tailed) | .310 | .010 | .000 | .496 | .143 | .001 |

| | | | presence of regression | mitotic rate | melanoma subtype | multiple melanoma | Breslow thickness | total number of AAbs (out of 139) |
|---|---|---|---|---|---|---|---|---|
| Spearman's rho | serum scores (top 139 markers) | Correlation Coefficient | .053 | .100 | −.009 | .078 | .095 | .776** |
| | | Sig (2-tailed) | .595 | .310 | .931 | .429 | .369 | .000 |
| | | N | 104 | 104 | 104 | 104 | 92 | 104 |
| | age in years | Correlation Coefficient | −.123 | .253** | .090 | .362** | .197 | −.086 |
| | | Sig (2-tailed) | .213 | .010 | .364 | .000 | .060 | .387 |
| | | N | 104 | 104 | 104 | 104 | 104 | 104 |

TABLE 5-continued

| | | | | | | | |
|---|---|---|---|---|---|---|---|
| TNM stage | Correlation Coefficient | −.123 | .253** | .090 | .362** | .197 | −.086 |
| | Sig (2-tailed) | .506 | .000 | .255 | .103 | .000 | .495 |
| | N | 104 | 104 | 104 | 104 | 104 | 104 |
| gender | Correlation Coefficient | −.233* | .067 | −.017 | −.116 | .086 | −.035 |
| | Sig (2-tailed) | .506 | .000 | .255 | .103 | .000 | .495 |
| | N | 104 | 104 | 104 | 104 | 104 | 104 |
| tumour site | Correlation Coefficient | .095 | −.144 | .022 | −.125 | .052 | −.066 |
| | Sig (2-tailed) | .340 | .143 | .821 | .207 | .621 | .308 |
| | N | 104 | 104 | 104 | 104 | 104 | 104 |
| presence of ulceration | Correlation Coefficient | .245* | −.327** | .296** | −.086 | −.213* | −.042 |
| | Sig (2-tailed) | .012 | .001 | .002 | .384 | .041 | .675 |
| | N | 104 | 104 | 104 | 104 | 104 | 104 |
| presence of pregression | Correlation Coefficient | 1.000 | −.123 | .067 | −.304** | −.037 | .103 |
| | Sig (2-tailed) | — | .183 | .498 | .002 | .723 | .296 |
| | N | 104 | 104 | 104 | 104 | 104 | 104 |
| miotic rate | Correlation Coefficient | −.132 | 1.000 | .049 | .143 | .500** | .165 |
| | Sig (2-tailed) | .183 | — | .620 | .147 | .000 | .093 |

Figure 3:
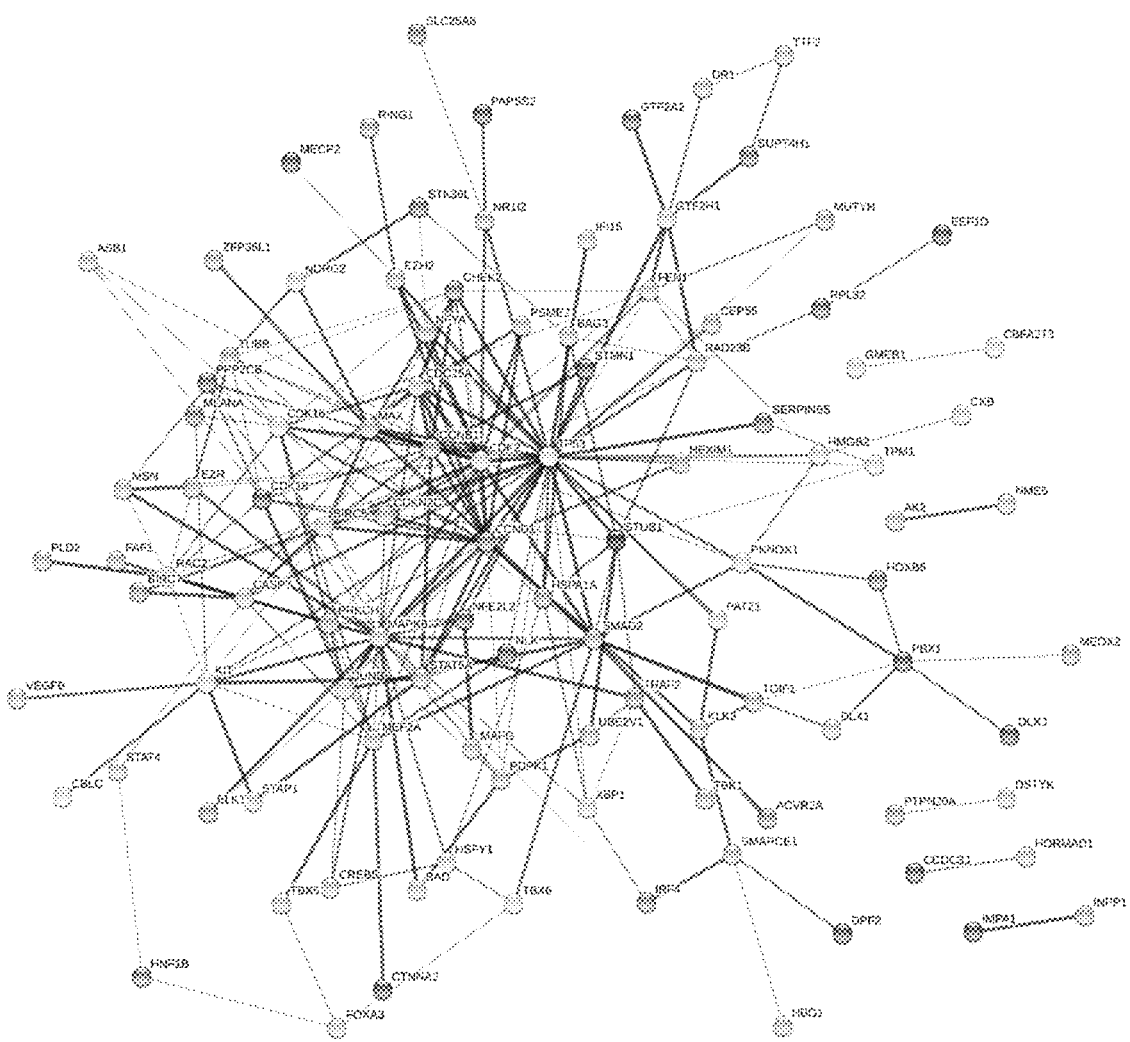
FIG. 3 is a schematic representation of the protein interaction network for the top 139 individual melanoma-associated biomarkers. The thickness of the line indicates the level of confidence. Proteins without any identified interactions were not included in this schematic.

(B) Melanoma-Associated Autoantibodies are Functionally Correlated with Cancer Pathways Associated with Melanomagenesis A STRING protein association network of the top 139 antigens was generated (FIG. 3). Interestingly, the majority of the seroreactive proteins are antigens intracellular proteins (101/139) of which the majority are contained within the nucleus (88/139), a cellular location that is usually protected from immune surveillance cells. Many cancer autoantibody studies have however also reported detection of AAbs against nuclear antigens in other cancers and this has been suggested to be due to spillage of the intracellular contents into the surrounding tissue following cell death in cancer (Zaenker et al., supra). Furthermore, the top 139 identified biomarkers appear related to primarily to general cancer pathways, apoptosis, pathways associated with the immune response and cell cycle, p53 signalling and the MAPK signalling pathway, the main pathway associated with melanomagenesis, highlighting the biological relevance of the identified biomarkers.

(C) The Expression of a Combination of the Anti-ZBTB7B, Anti-PRKCH, Anti-TP53, Anti-PCTK1, Anti-PQBP1, Anti-UBE2V1, Anti-IRF4, Anti-MAPK8_Tv2, Anti-MSN and Anti-TPM1 Autoantibodies Correlates with Early Stage Melanoma Since the development of a diagnostic blood test that is comprised of 139 biomarkers is impractical and hence not clinically applicable, we utilised a two stage analysis approach involving random forest and classification tree analysis to identify a combination of 10 biomarkers or less with the highest diagnostic potential.

Figure 4:
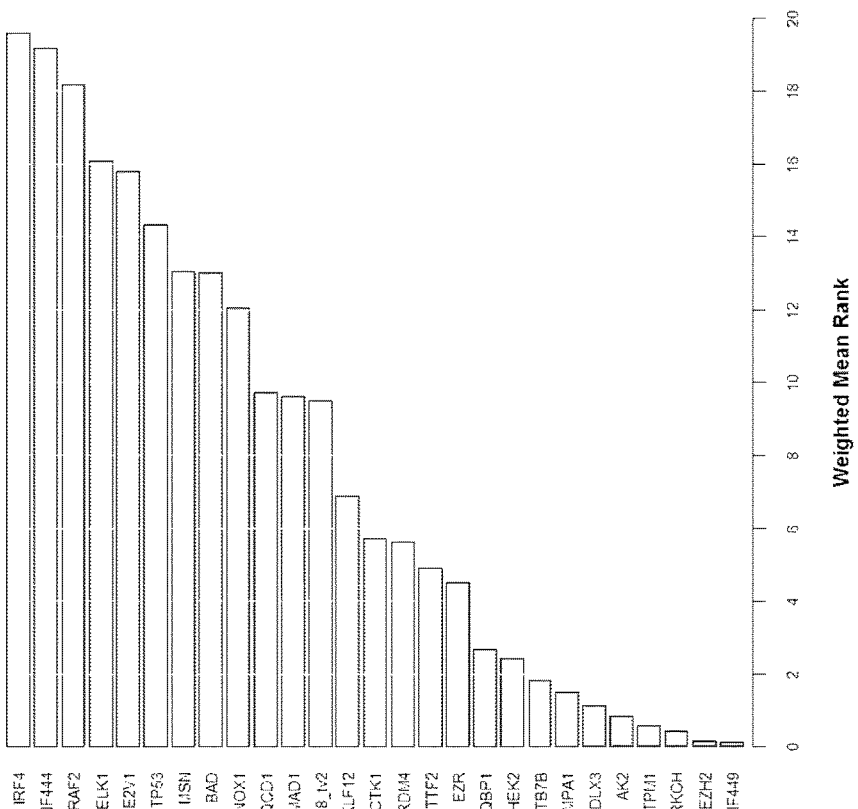
FIG. 4 is a graphical representation of (A) inclusion frequency (%; x-axis) and (B) weighted mean rank (x-axis) for the 20 most frequently included autoantibody biomarkers in the 1000 random forest analysis.
Figure 4:
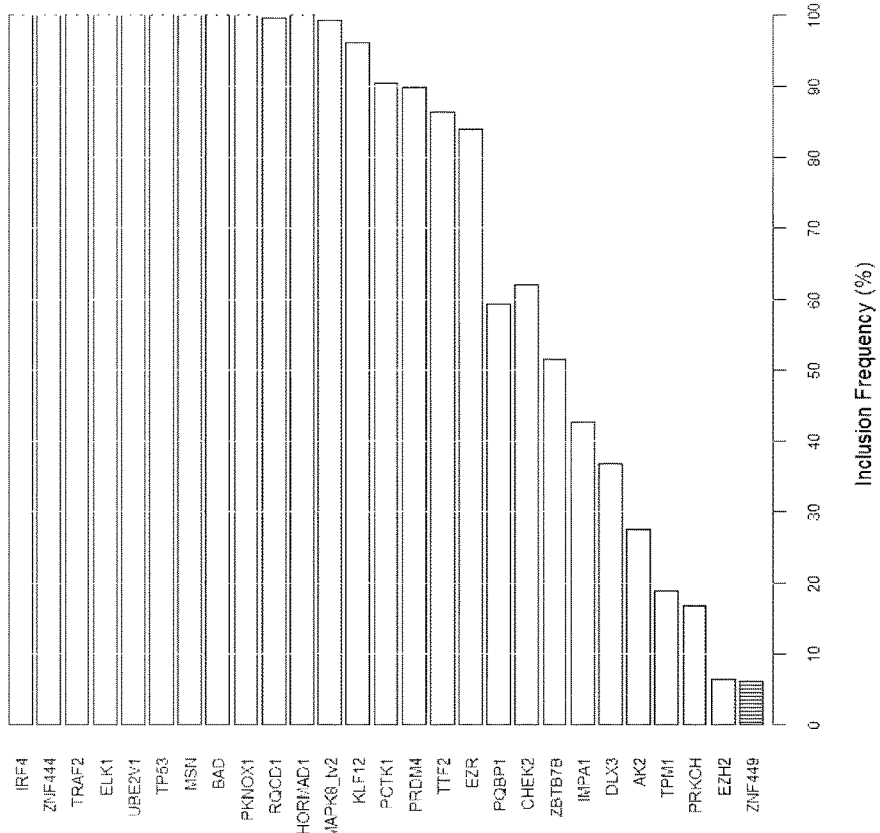
Figure 5:
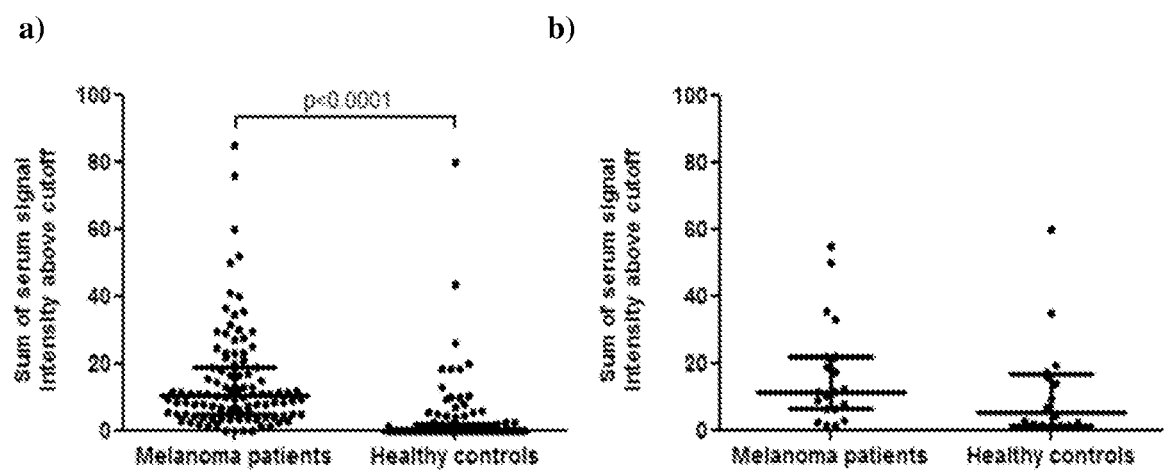
FIG. 5 is a graphical representation of serum scores (y-axis) in melanoma patients and healthy controls (x-axis) for the 27 melanoma-associated biomarkers with the highest weighted mean rank score in (A) cohort 1 and (B) cohort 2.

Following random forest analysis of the data from cohort 1, the top 20 most influential markers for a diagnostic model were identified with the most important AAbs were given a rank score of 20 and the least important marker given a score of 1. This analysis was repeated 1000 times to generate 1000 random forests. When the top 20 markers of each of these 1000 forests were combined, a list of 27 unique biomarkers and their percent model inclusion frequency (FIG. 4A), with potential to aid in melanoma diagnosis, were identified. The number and proportion of the appearance of each of these biomarkers in the 1000 top 20 AAb lists was then multiplied by the average rank score to obtain a weighted mean rank by which the overall importance of the biomarker for melanoma diagnosis was determined. A sorted list of the most important biomarkers and their corresponding weighted mean rank scores are shown in FIG. 4B. In cohort 1, patient serum scores for these 27 antigens were again significantly higher with a median of 10.2 (IQR 4.7-19.1), than the healthy control median serum score of 0 (IQR 0-1.6, p<0.0001, FIG. 5A) while, possibly due to the low sample size, there was no significant difference between patient and controls serum scores in cohort 2 (median of 11.2 (IQR 6.2-22.0) versus 5.5 (1.4-16.9), p=0.176, FIG. 5B). Interferon regulator 4 (IRF4) was the most frequently included biomarker in the 1000 combinations that displayed the highest average rank score and was therefore the most important marker to contribute to the overall sensitivity and specificity in a combination of AAbs. As a single biomarker, IRF4 displayed a sensitivity of 5.8% at 100% specificity.

Figure 6:
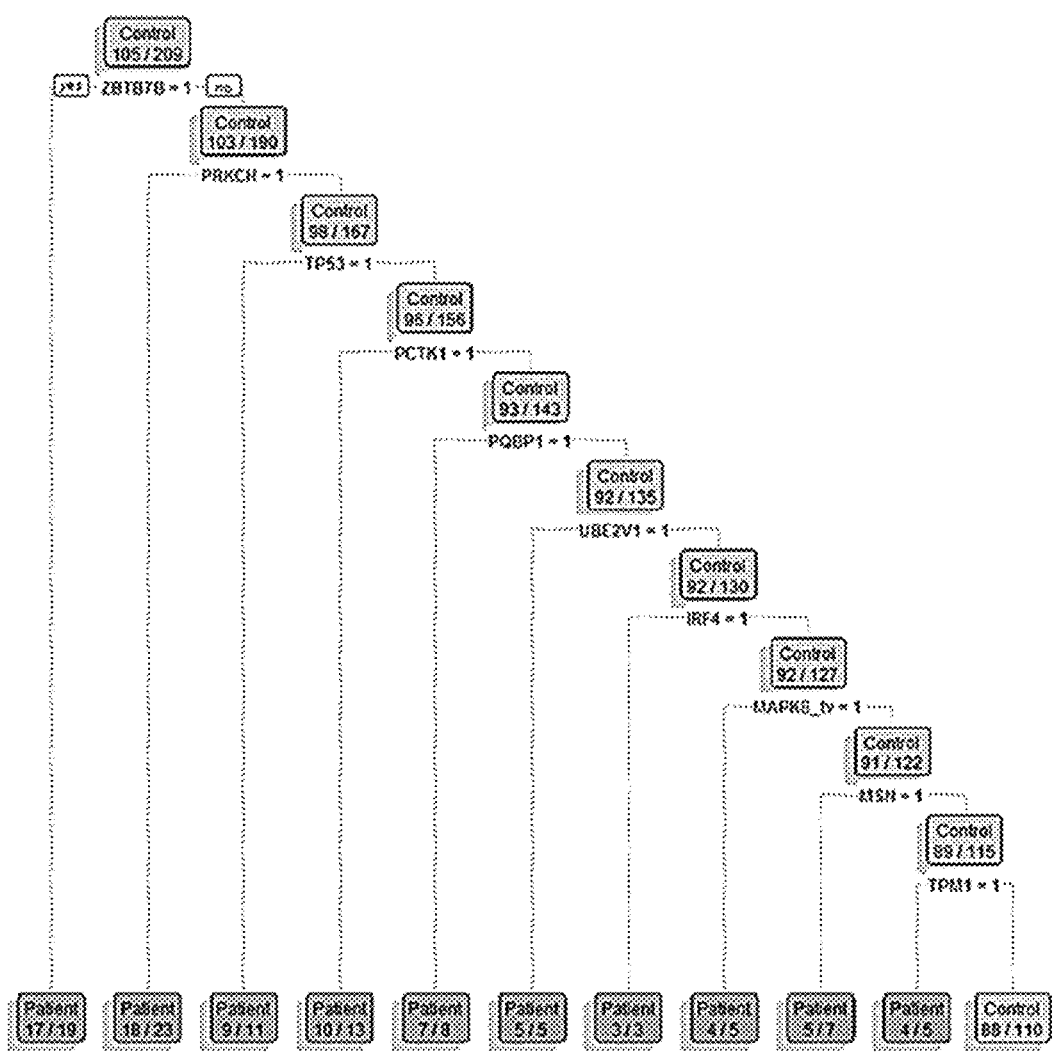
FIG. 6 is a schematic representation of the regression analysis of the best combination of the identified autoantibody biomarkers. Melanoma patients are represented by red boxes and healthy controls are blue boxes.

Classification tree analysis was then applied to these 27 biomarkers and showed that the best combination of biomarkers ensuring an increased sensitivity and specificity for melanoma diagnosis, is a signature of 10 AAbs, including anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 (FIG. 6), with a combined sensitivity of 79%, specificity of 84% and an AUC of 0.828 (FIGS. 7 and 8). The biomarkers included in the panel did not necessarily display the highest individual diagnostic potential (Table 3). Instead, they are a combination, displaying a broader occurrence of positive seroreactivity for patient sera if a positive diagnosis is said to be represented by positive seroreactivity with at least one or more of the biomarkers in the combination.

Unlike other autoantibodies that have been suggested to be suitable prognostic biomarkers for melanoma, this is the first study to investigate the presence of AAbs in early stage melanoma. Furthermore, no previous studies have utilised a screening approach using the individual patient autoimmune repertoire against an unbiased array of proteins. Therefore, the inventors have been the first to identify AAbs as diagnostic biomarkers in a large cohort of primary melanoma patients compared to healthy volunteers using a high-throughput functional microarray platform.

The invention claimed is:

1. A method of treating a subject with melanoma, wherein the melanoma is Stage 0, Stage I or Stage II melanoma, the method comprising the steps of:
   a. measuring the expression levels of a group of autoantibodies including anti-ZBTB7B, anti-PRKCH, anti-TP53, anti-PCTK1, anti-PQBP1, anti-UBE2V1, anti-IRF4, anti-MAPK8_tv2, anti-MSN and anti-TPM1 in a biological sample obtained from a subject;
   b. comparing the levels of expressions of all of the autoantibodies in the group in the biological sample to reference values, wherein the reference values are representative of known or predetermined levels of the same autoantibodies in a reference sample or a plurality of reference samples from a subject or subjects that have never been diagnosed with cancer, melanoma or an autoimmune disease, wherein the expression levels of all of the autoantibodies in the group in the biological sample greater than the reference value provides an indication that the subject has melanoma;
   c. identifying a subject that has melanoma from step (b); and
   d. treating the subject identified in step (c) as having melanoma with a therapeutic regimen for preventing or delaying the progression of the melanoma, wherein the therapeutic regimen is selected from the group consisting of surgery, administration of a chemotherapeutic agent, radiotherapy, immunotherapy and targeted molecular therapy.

2. The method of claim 1, wherein the step of measuring the expression levels of the autoantibodies in the biological sample comprises measuring the levels of protein expression of the autoantibodies in the biological sample.

3. The method of claim 2, wherein the levels of protein expression are measured using multiplexed protein expression analysis.

4. The method of claim 3, wherein the multiplexed protein expression analysis method is protein microarray or Luminex bead array.

5. The method of claim 1, wherein the biological sample is a blood sample or a component of the blood sample.

6. The method of claim 5, wherein the component of the blood sample is serum.

7. The method of claim 5, wherein the component of the blood sample is plasma.

8. The method of claim 1, wherein the therapeutic regimen comprises surgery.

9. The method of claim 8, wherein the therapeutic regimen further comprises the administration of one or more or all of a chemotherapeutic agent, radiotherapy, immunotherapy and targeted molecular therapy.

* * * * *